United States Patent
Tsutsui et al.

(10) Patent No.: US 10,512,528 B2
(45) Date of Patent: Dec. 24, 2019

(54) NON-CONTACT POWER SUPPLY DEVICE

(71) Applicant: PANASONIC INTELLECTUAL PROPERTY MANAGEMENT CO., LTD., Osaka (JP)

(72) Inventors: Mami Tsutsui, Shiga (JP); Hiroyasu Kitamura, Shiga (JP); Norihiro Iwamura, Shiga (JP); Seiichi Iwao, Shiga (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 180 days.

(21) Appl. No.: 15/563,499

(22) PCT Filed: Mar. 23, 2016

(86) PCT No.: PCT/JP2016/001679
§ 371 (c)(1),
(2) Date: Sep. 29, 2017

(87) PCT Pub. No.: WO2016/163092
PCT Pub. Date: Oct. 13, 2016

(65) Prior Publication Data
US 2018/0085206 A1  Mar. 29, 2018

(30) Foreign Application Priority Data
Apr. 6, 2015 (JP) ................................. 2015-078055

(51) Int. Cl.
H02J 7/00 (2006.01)
H02J 7/14 (2006.01)
(Continued)

(52) U.S. Cl.
CPC ............. *A61C 17/22* (2013.01); *H01F 38/14* (2013.01); *H02J 7/025* (2013.01); *H02J 50/12* (2016.02)

(58) Field of Classification Search
USPC ... 320/107, 108, 134, 17, 137, 16, 115, 139, 320/145, 142
See application file for complete search history.

(56) References Cited

U.S. PATENT DOCUMENTS

| 5,991,170 A | 11/1999 | Nagai et al. |
| 2010/0219696 A1 | 9/2010 | Kojima |

(Continued)

FOREIGN PATENT DOCUMENTS

| JP | 2002-152997 A | 5/2002 |
| JP | 2010-200571 A | 9/2010 |

(Continued)

OTHER PUBLICATIONS

International Search Report and Written Opinion issued in International Patent Application No. PCT/JP2016/001679, dated Jun. 7, 2016; with partial English translation.

*Primary Examiner* — Alexis B Pacheco
(74) *Attorney, Agent, or Firm* — McDermott Will & Emery LLP

(57) ABSTRACT

A noncontact power supply device includes a power transmission device, a magnetism collecting device, and a power reception device. The power transmission device includes switching elements that make a power-transmission resonant circuit generate an alternating magnetic flux from a power source circuit. The power reception device includes a magnetism collecting device having a magnetism collecting circuit not connected to a load, a power receiving coil which is capable of being magnetically coupled to the magnetism collecting device, and a rectifier circuit that supplies output power of the power receiving coil to a load. A power- (Continued)

transmission resonance frequency of the power-transmission resonant circuit is smaller than a drive frequency of each of switching elements, and a power-reception resonance frequency of the magnetism collecting circuit is larger than the drive frequency of each of switching elements. Accordingly, the present invention provides a noncontact power supply device with high power transmission efficiency and with excellent productivity.

11 Claims, 18 Drawing Sheets

(51) Int. Cl.
    *A61C 17/22*     (2006.01)
    *H01F 38/14*     (2006.01)
    *H02J 50/12*     (2016.01)
    *H02J 7/02*     (2016.01)

(56) References Cited

U.S. PATENT DOCUMENTS

| | | | | |
|---|---|---|---|---|
| 2012/0043825 A1* | 2/2012 | Urano | .................... | H02J 5/005 307/104 |
| 2014/0091756 A1* | 4/2014 | Ofstein | .................... | H02J 5/005 320/108 |
| 2014/0239736 A1* | 8/2014 | Kai | .................... | H04B 5/0037 307/104 |
| 2015/0015087 A1* | 1/2015 | Endo | .................... | H01F 38/14 307/104 |
| 2015/0255994 A1* | 9/2015 | Kesler | .................... | H02J 5/005 307/10.1 |
| 2015/0263528 A1 | 9/2015 | Kitamura et al. | | |
| 2015/0371771 A1* | 12/2015 | Abu Qahouq | .................... | H04B 5/0087 307/104 |
| 2017/0047786 A1* | 2/2017 | Park | .................... | H02J 7/02 |

FOREIGN PATENT DOCUMENTS

| | | |
|---|---|---|
| JP | 2012-050209 A | 3/2012 |
| JP | 2013-055871 A | 3/2013 |
| JP | 2014-036545 A | 2/2014 |
| JP | 2015-002643 A | 1/2015 |
| WO | 98/034319 A1 | 8/1998 |

\* cited by examiner

FIG. 3
FIG. 4
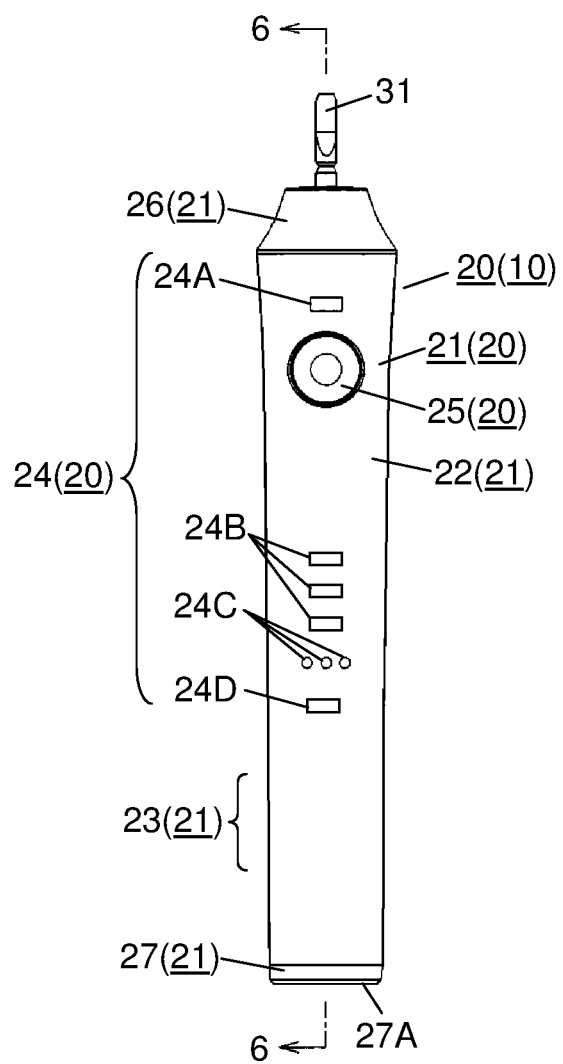
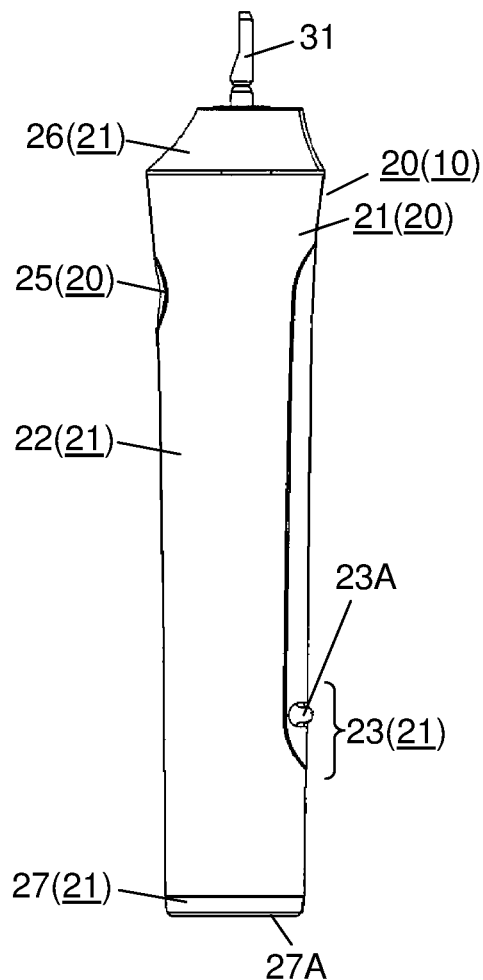

FIG. 6
FIG. 7
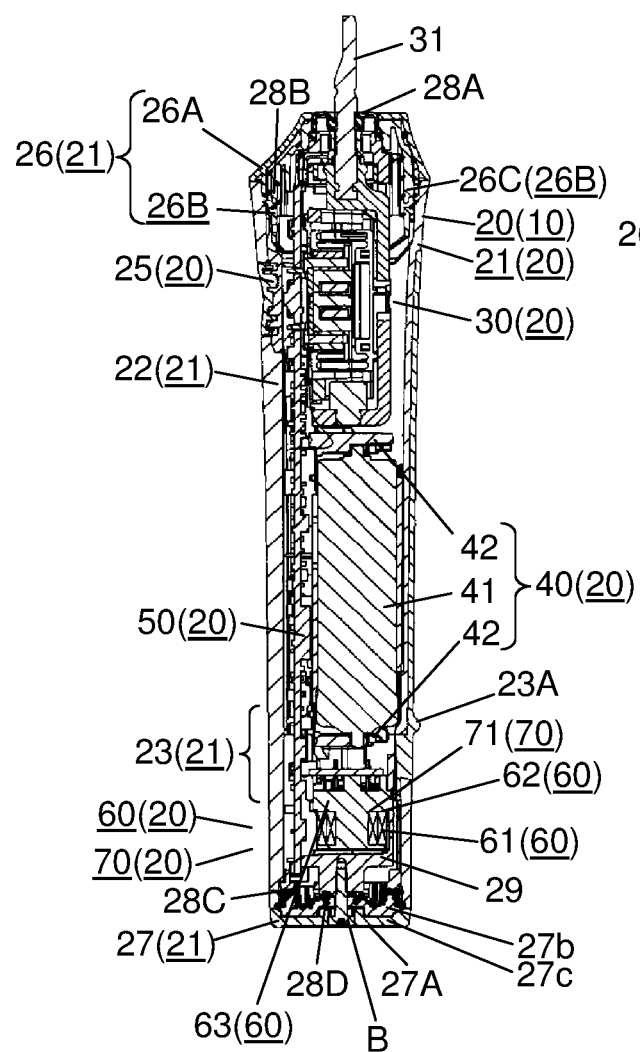
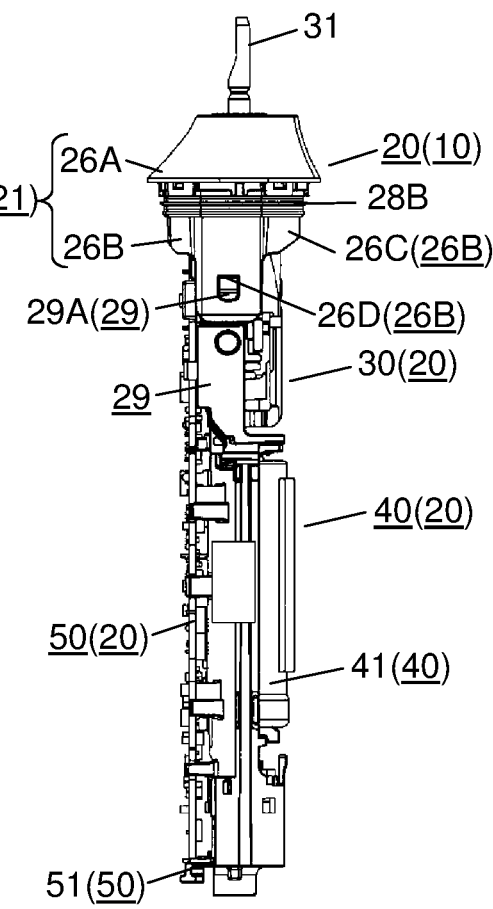

NON-CONTACT POWER SUPPLY DEVICE

RELATED APPLICATIONS

This application is the U.S. National Phase under 35 U.S.C. § 371 of International Patent Application No. PCT/JP2016/001679, filed on Mar. 23, 2016, which in turn claims the benefit of Japanese Application No. 2015-078055, filed on Apr. 6, 2015, the entire disclosures of which Applications are incorporated by reference herein.

TECHNICAL FIELD

The present invention relates to a noncontact power supply device.

BACKGROUND ART

A conventional noncontact power supply device includes a power transmission device that transmits power by a magnetic flux, and a power reception device that receives the magnetic flux which is output from the power transmission device. The power transmission device includes a power-transmission resonant circuit, and a plurality of switching elements. The power-transmission resonant circuit outputs an alternating magnetic flux to the power reception device by alternating power supplied from a power source circuit. The plurality of switching elements perform a switching operation for making the power-transmission resonant circuit generate the alternating magnetic flux. The power reception device includes a power receiving coil and a rectifier circuit. The power receiving coil is magnetically coupled to the power-transmission resonant circuit. The rectifier circuit supplies the power output from the power receiving coil to a load.

In this case, it is generally known that when a drive frequency of each switching element, a resonance frequency of the power-transmission resonant circuit, and a resonance frequency of the power receiving coil are substantially coincided with each other, power transmission efficiency from the power transmission device to the power reception device improves. Therefore, there is disclosed a noncontact power supply device in which a power transmission device and a power reception device are designed such that the above relationship is established (for example, refer to PTL 1).

However, values of elements configuring a circuit of the noncontact power supply device vary at a manufacturing time. Therefore, at least one of the drive frequency and each resonance frequency is deviated from a design value in some cases. Accordingly, in manufacturing a noncontact power supply device having high transmission efficiency by preventing a deviation from a design value of each element, there is a concern about reduction in productivity. On the other hand, power transmission efficiency is one of main factors required for the noncontact power supply device. Therefore, it is not preferable to sacrifice power transmission efficiency as a result of prioritizing the productivity.

CITATION LIST

Patent Literature

PTL 1: Unexamined Japanese Patent Publication No. 2002-152997

SUMMARY OF THE INVENTION

The present invention provides a noncontact power supply device with high power transmission efficiency and with excellent productivity.

Specifically, one exemplary embodiment of the present invention provides a noncontact power supply device having a power transmission device including a power-transmission resonant circuit that outputs an alternating magnetic flux by alternating power supplied from a power source circuit; and a switching element that makes the power-transmission resonant circuit generate an alternating magnetic flux. The noncontact power supply device further has: a magnetism collecting device including: a magnetism collecting circuit configuring a magnetism-collecting resonant circuit which is capable of being magnetically coupled to the power-transmission resonant circuit and is not electrically connected to a load; and a power reception device including a power receiving coil which is capable of being magnetically coupled to the magnetism collecting circuit, and a rectifier circuit which is capable of supplying power output from the power reception device to the load. A power-transmission resonance frequency of the power-transmission resonant circuit is smaller than the drive frequency of the switching element, and the power-reception resonance frequency of the magnetism collecting circuit is larger than the drive frequency of the switching element.

Further, a noncontact power supply device according to one exemplary embodiment of the present invention has a power transmission device including: a power-transmission resonant circuit that outputs an alternating magnetic flux by alternating power supplied from a power source circuit; and a switching element that makes the power-transmission resonant circuit generate an alternating magnetic flux. The noncontact power supply device further has a power reception device including: a power receiving coil which is capable of being magnetically coupled to the power-transmission resonant circuit; and a rectifier circuit which is capable of supplying power output from the power receiving coil to a load. Further, a power-transmission resonance frequency of the power-transmission resonant circuit is smaller than the drive frequency of the switching element, and a power-reception resonance frequency of the power-reception resonant circuit including the power receiving coil is larger than the drive frequency of the switching element.

BRIEF DESCRIPTION OF DRAWINGS

FIG. 3 is a front view of the electric toothbrush in FIG. 2.

FIG. 4 is a side view of the electric toothbrush in FIG. 2.

FIG. 6 is a cross-sectional view taken along line 6-6 in FIG. 3.

FIG. 7 is a side view of the electric toothbrush from which a grip part and a lower cap in FIG. 2 are removed.

DESCRIPTION OF EMBODIMENT

Figure 1:
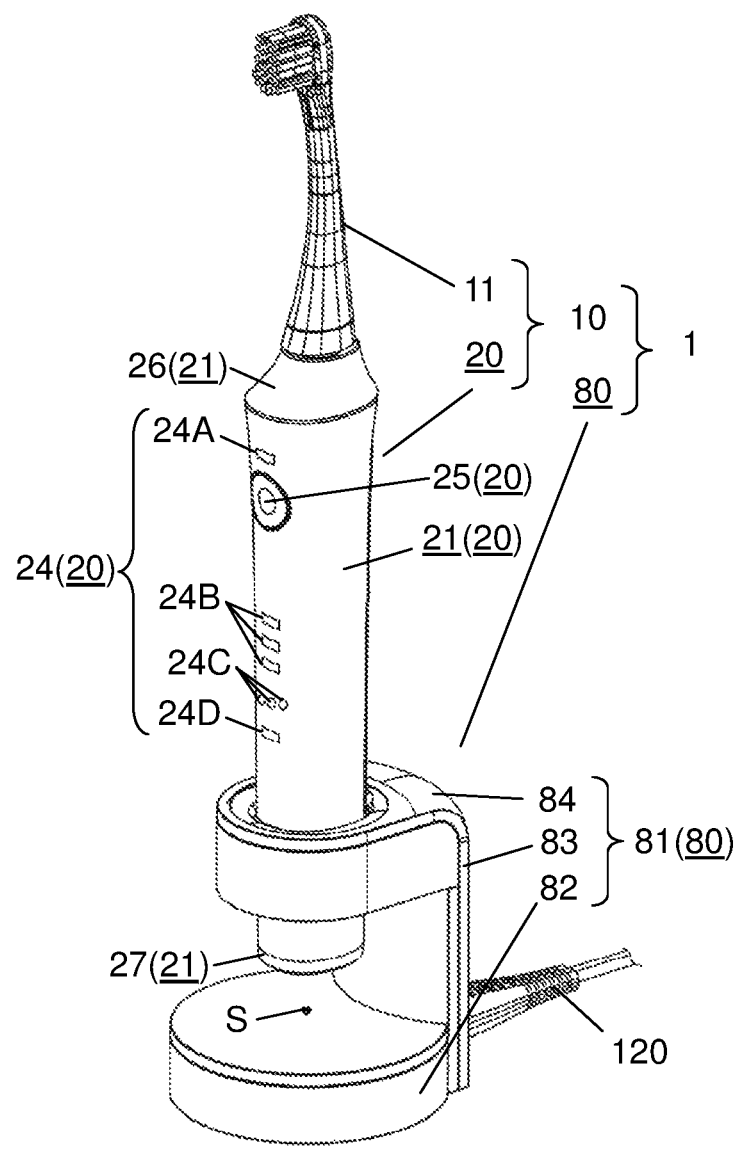
FIG. 1 is a perspective view of a noncontact power supply device according to the present exemplary embodiment.

Hereinafter, an exemplary embodiment of the present invention will be described with reference to the drawings. In the following description, the same reference numerals are attached to the same or corresponding parts, and redundant description will be omitted. The present invention is not limited by the present exemplary embodiment.

Exemplary Embodiment

Hereinafter, a configuration of a noncontact power supply device according to the present exemplary embodiment will be described with reference to FIG. 1 to FIG. 20, mainly, FIG. 1 to FIG. 8.

As shown in FIG. 1, noncontact power supply device 1 of the present exemplary embodiment includes a small electric device and charging stand 80. In the following, for the small electric device, electric toothbrush 10 which is an oral hygiene device will be described as an example.

Electric toothbrush 10 includes body 20 in a columnar shape, and head 11 detachably attached to output shaft 31 (refer to FIG. 2) of drive unit 30 (refer to FIG. 6) of body 20.

Figure 2:
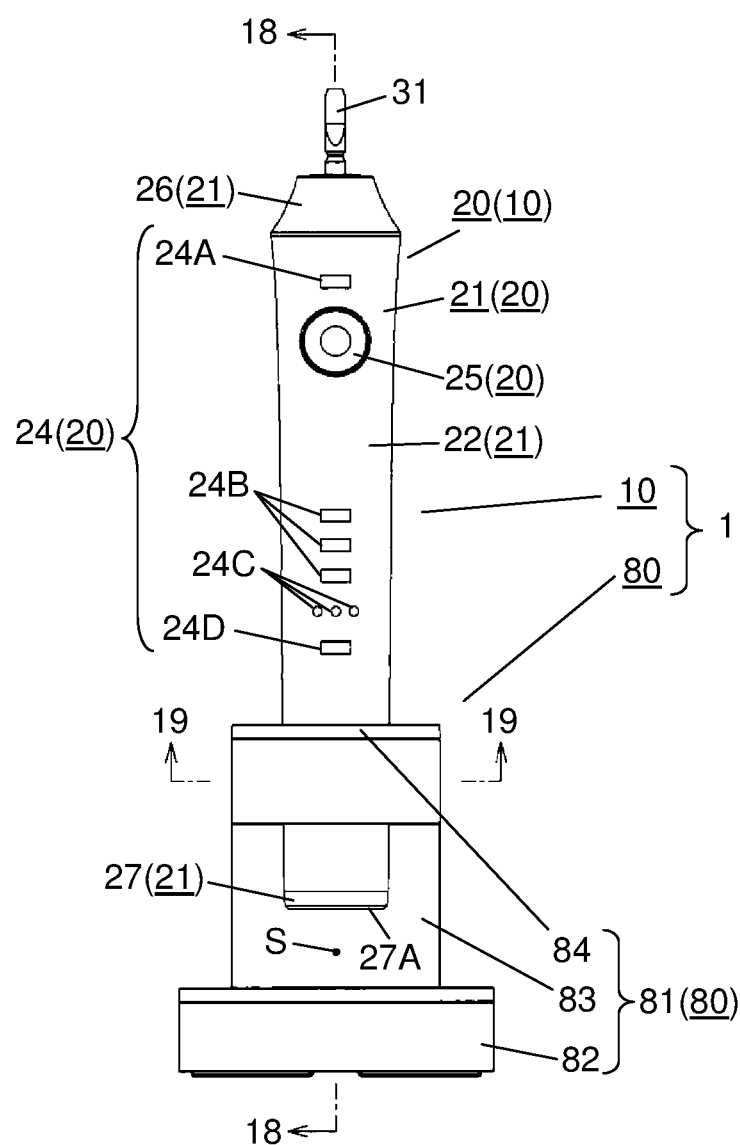
FIG. 2 is a front view of the noncontact power supply device from which a head of an electric toothbrush in FIG. 1 is removed.

Body 20 includes case 21, display unit 24, and power source button 25 shown in FIG. 2, support body 29, drive unit 30, power source unit 40, and substrate 50 shown in FIG. 7, and power reception device 60 and magnetism collecting device 70 shown in FIG. 6. Drive unit 30, power source unit 40, substrate 50, power reception device 60, and magnetism collecting device 70 are supported by support body 29, and are accommodated inside case 21.

Case 21, as shown in FIG. 3, has grip part 22 in a hollow structure, upper cap 26 that closes an upper part of grip part 22, and lower cap 27 that closes a lower part of grip part 22.

Figure 19:
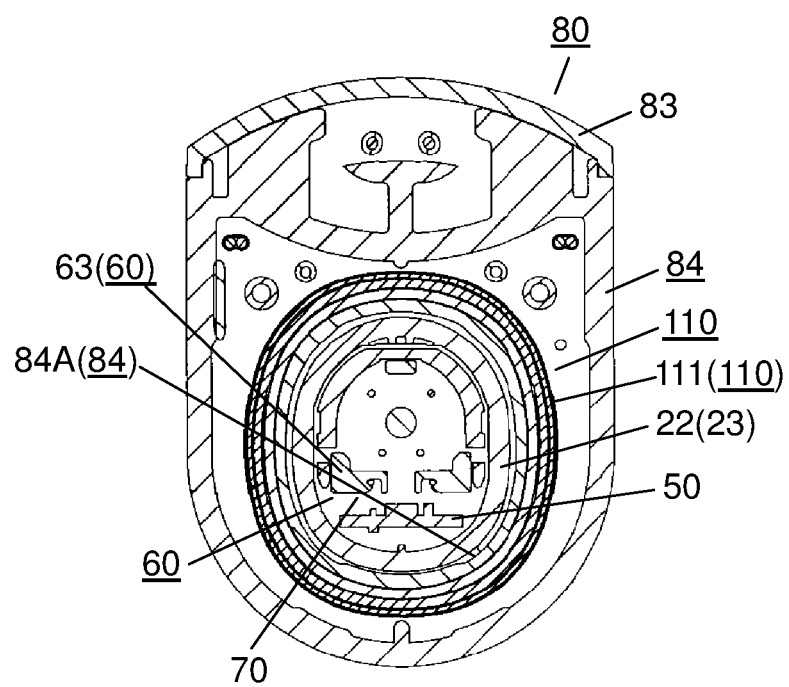
FIG. 19 is a cross-sectional view taken along line 19-19 in FIG. 2.

Grip part 22 includes a tapered shape in which an outer diameter becomes smaller from upper cap 26 toward lower cap 27. Specifically, grip part 22, includes a cross section along a width direction, in a substantially elliptical shape (including an elliptical shape), as shown in FIG. 19.

Figure 5:
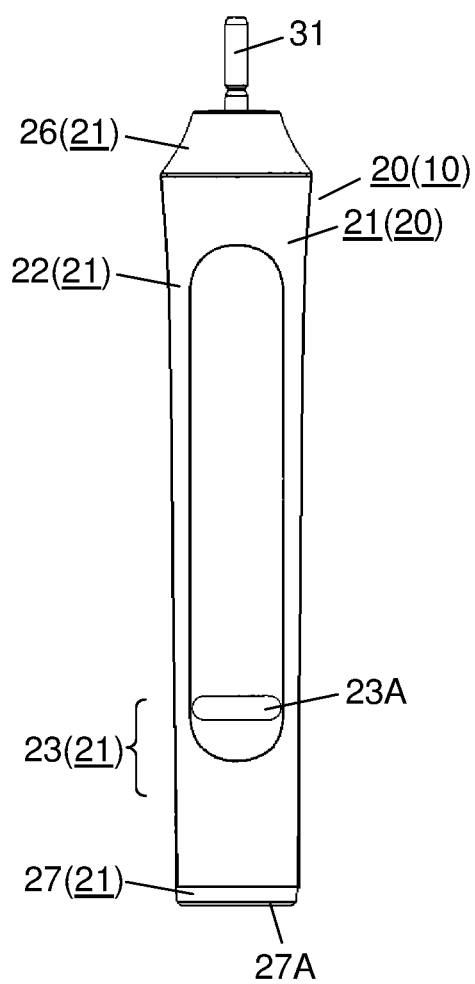
FIG. 5 is a rear view of the electric toothbrush in FIG. 2.

As shown in FIG. 4 and FIG. 5, grip part 22 includes protrusion 23A protruding outward from grip part 22, on the rear surface. Protrusion 23A is extended in a peripheral direction of grip part 22. Further, protrusion 23A is discontinuously formed in a peripheral direction of grip part 22.

Further, grip part 22 includes supported part 23 at a lower portion than protrusion 23A, with protrusion 23A as an upper end. Supported part 23 is covered with support part 84 of charging stand 80, when grip part 22 is supported by charging stand 80 (refer to FIG. 2).

Upper cap 26 of case 21 includes front cap 26A and inner cap 26B superposed on an inner side of front cap 26A, as shown in FIG. 6. Upper cap 26 is fitted to an upper part of grip part 22.

Inner cap 26B, as shown in FIG. 7, includes coupling part 26C in a circular cylindrical shape protruding downward. Hole 26D is formed in coupling part 26C.

Figure 8:
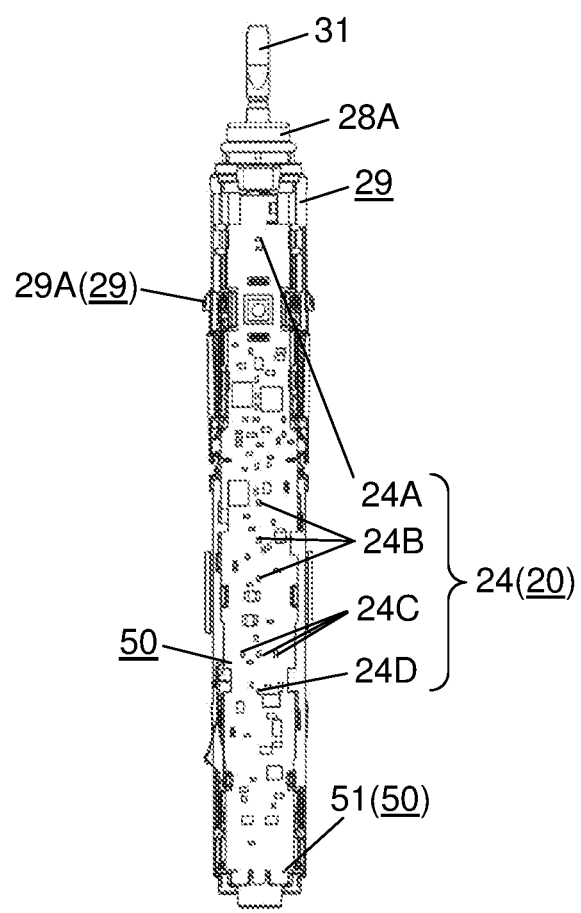
FIG. 8 is a front view of the electric toothbrush from which the grip part, an upper cap, and the lower cap in FIG. 2 are removed.
Figure 9:
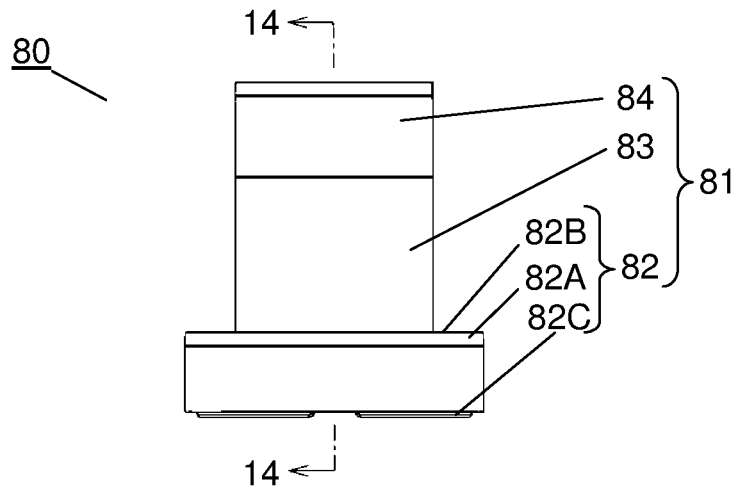
FIG. 9 is a front view of a charging stand in FIG. 1.

Upper cap 26 is attached with disk-shaped elastic member 28A on an upper surface, as shown in FIG. 8. Output shaft 31 of drive unit 30 described later is provided so as to protrude from elastic member 28A. As shown in FIG. 6 and FIG. 7, between upper cap 26 and an inner periphery of grip part 22, elastic member 28B formed of an O-ring, for example, is attached.

Upper cap 26 is attached to support body 29, by being fitted to hook 29A in which hole 26D of coupling part 26C is formed on an outer periphery of support body 29.

Lower cap 27 has a double structure of front cap 27C and inner cap 27B, as shown in FIG. 6. Lower cap 27 is fitted to a lower part of grip part 22. Then, lower cap 27 is attached to support body 29 by screwing screw B from below. Between lower cap 27 and the inner periphery of grip part 22, elastic member 28C formed of an O-ring, for example, is attached. Similarly, between lower cap 27 and a bottom surface of support body 29, elastic member 28D such as an O-ring is attached.

Elastic members 28A to 28D prevent water from entering the inside of case 21 and vibration inside body 20 from being transmitted to case 21. Further, the double structure of upper cap 26 and lower cap 27 prevents water from entering the inside of case 21 and vibration generated inside body 20 from being transmitted to case 21.

Support body 29 attached with upper cap 26, drive unit 30, power source unit 40, substrate 50, and power reception device 60 is inserted into an opening at an upper part of grip part 22. Then, lower cap 27 is attached and is screwed with screw B from below grip part 22. As a result, body 20 of electric toothbrush 10 is assembled.

Further, as shown in FIG. 3, display unit 24 is provided in body 20 to enable a user to visually recognize display unit 24. Display unit 24 includes ion display unit 24A, drive-mode display unit 24B, residual-quantity display unit 24C, and charge display unit 24D. Ion display unit 24A displays by lighting that head 11 is generating ion. Drive-mode display unit 24B displays while changing a lighting state, for example, according to a kind (a mode) of vibration of head 11. A kind of vibration of head 11 is controlled by a drive mode of drive unit 30 (refer to FIG. 6). Residual-quantity display unit 24C displays a residual capacity and the like, according to a voltage of rechargeable battery 41 (refer to FIG. 6) of power source unit 40.

Display unit 24 is configured, for example, with an LED (Light Emitting Diode) that is mounted on substrate 50, as shown in FIG. 8.

In this case, grip part 22 is formed of a material of high light transmittance at a portion opposite to display unit 24 to enable the user to visually recognize a lighting state of display unit 24. In this case, a hole may be formed in grip part 22 such that at least a part of display unit 24 is exposed from a surface of grip part 22.

Further, display unit 24 is disposed at a different position from supported part 23 of body 20, for example, at an opposite side. Therefore, as shown in FIG. 2, even when body 20 is supported by charging stand 80, the user can visually recognize the lighting state of display unit 24. Particularly, by visually recognizing charge display unit 24D, the user can easily grasp whether electric toothbrush 10 is being charged.

Power source button 25 is attached to body 20 such that the user can operate power source button 25. Power source button 25 is provided in body 20 such that at least a part of power source button protrudes through the surface of grip part 22. When the user presses power source button 25, a drive controller (not shown) starts driving head 11, based on a drive mode set in drive unit 30 (refer to FIG. 6).

Output shaft 31 of drive unit 30 is supported by body 20 in a state of protruding through elastic member 28A at an upper part of case 21, as shown in FIG. 6. Drive unit 30 is exemplified by an electric linear actuator, for example. When drive unit 30 is driven, output shaft 31 vibrates. Therefore, head 11 (refer to FIG. 1) attached to output shaft 31 vibrates. Accordingly, a predetermined operation (tooth brushing, for example) is performed on the user. Drive unit 30 may be configured as an electric motor, and output shaft 31 may be configured as an eccentric shaft which is eccentric to a rotation axis of the electric motor. In this case, along with drive of the electric motor, the eccentric shaft as output shaft 31 vibrates. Accordingly, head 11 can be vibrated.

Power source unit 40 includes rechargeable battery 41 as a load of noncontact power supply device 1. For rechargeable battery 41, a secondary battery such as a lithium ion battery is exemplified, for example. An upper end and a lower end of rechargeable battery 41 are supported by metal plate 42 provided in support body 29. Power source unit 40 supplies power to drive unit 30.

Substrate 50 is disposed inside grip part 22 along inner periphery of grip part 22.

Power receiving unit 61 of power reception device 60 is disposed near bottom surface 27A inside grip part 22. Power receiving unit 61 includes power receiving coil 62 and magnetism collecting coil 71 of a magnetism collecting circuit that configures a magnetism-collecting resonant circuit of magnetism collecting device 70, as shown in FIG. 6. Power receiving coil 62 and magnetism collecting coil 71 are formed by being wound around bobbin-shaped magnetic core 63, for example. Power receiving coil 62 is wound around an outer periphery of magnetism collecting coil 71. Magnetic core 63 is attached to a base portion (a power-reception core holding portion) made of resin, with a core adhered to the base portion. Between magnetism collecting coil 71 and power receiving coil 62, an insulation tape not shown is wound for insulation. Power receiving coil 62 and an element configuring a circuit of substrate 50 are electrically connected to each other with lead frame 51 shown in FIG. 7. Lead frame 51 is provided at a lower end part of substrate 50, and supports substrate 50.

Above drive unit 30 is disposed near upper cap 26 inside grip part 22, as shown in FIG. 6. Similarly, power receiving coil 62 is disposed near lower cap 27. Further, power source unit 40 is disposed between drive unit 30 and power receiving coil 62.

As described above, electric toothbrush 10 as an example of a small electric device of noncontact power supply device 1 according to the present exemplary embodiment is configured.

Hereinafter, a configuration of charging stand 80 of noncontact power supply device 1 according to the present exemplary embodiment will be described with reference to FIG. 9 to FIG. 20.

Figure 14:
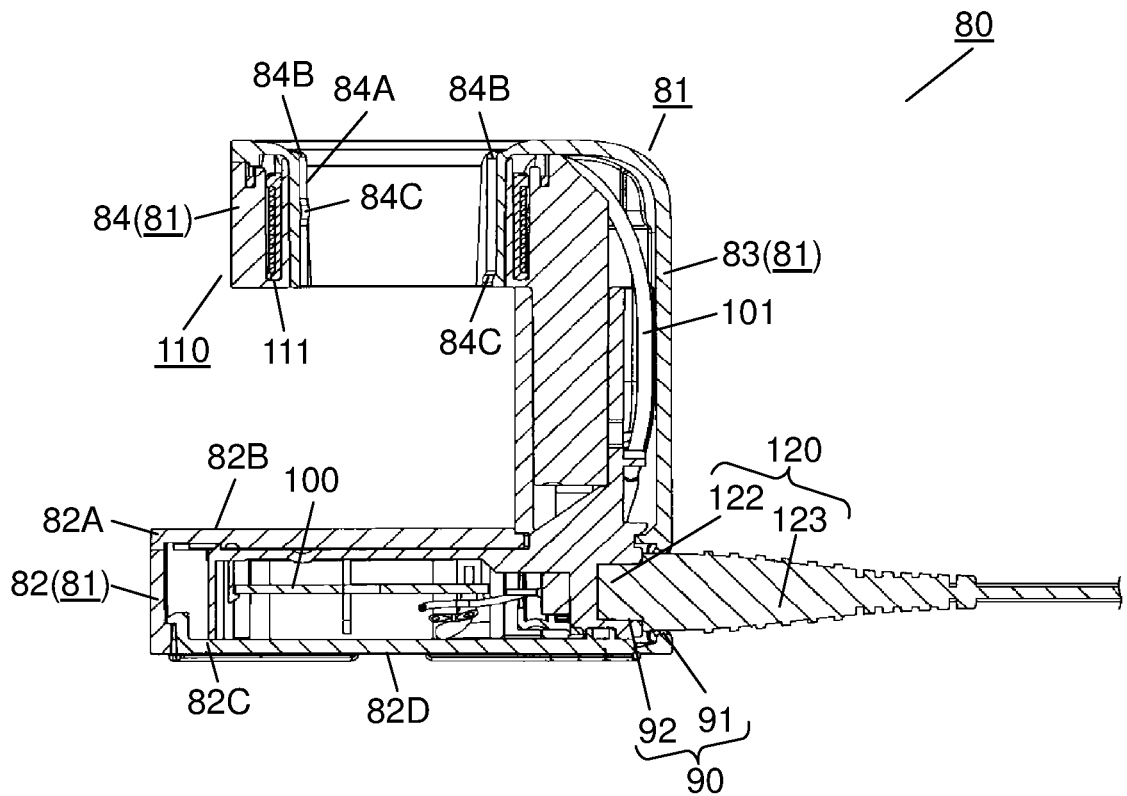
FIG. 14 is a cross-sectional view taken along line 14-14 in FIG. 9.

Charging stand 80 has case 81, connection part 90, substrate 100, and power transmission device 110, as shown in FIG. 14, for example. Connection part 90 is connected with power source line 120 for connection to alternating-current power source AC (refer to FIG. 21). Substrate 100 and power transmission device 110 are accommodated inside case 81.

Figure 10:
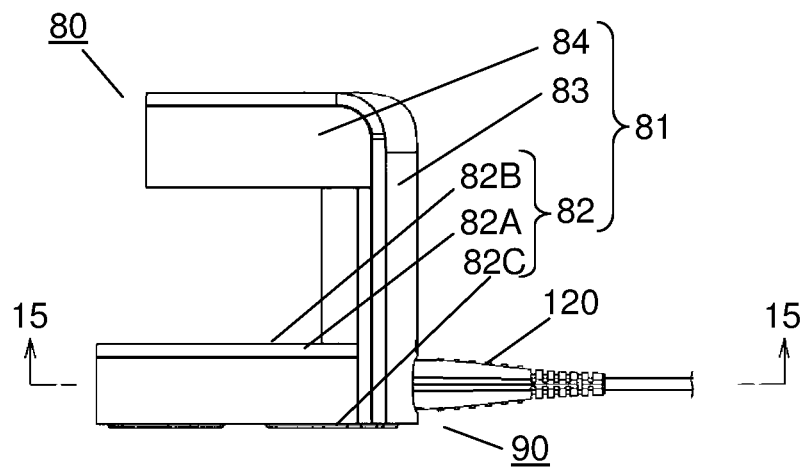
FIG. 10 is a side view of the charging stand in FIG. 1.

Case 81 has base 82, pillar 83, and support part 84. Base 82 is for setting case 81 on a setting surface of furniture or the like. Pillar 83 is provided so as to extend upward from a part of an outer peripheral part of base 82. Support part 84 is provided to protrude in a lateral direction (a horizontal direction) from an upper end of pillar 83. Support part 84 and base 82 are provided so as to extend in the same direction relative to pillar 83, as shown in FIG. 10. That is, support part 84 and base 82 are oppositely disposed.

Figure 12:
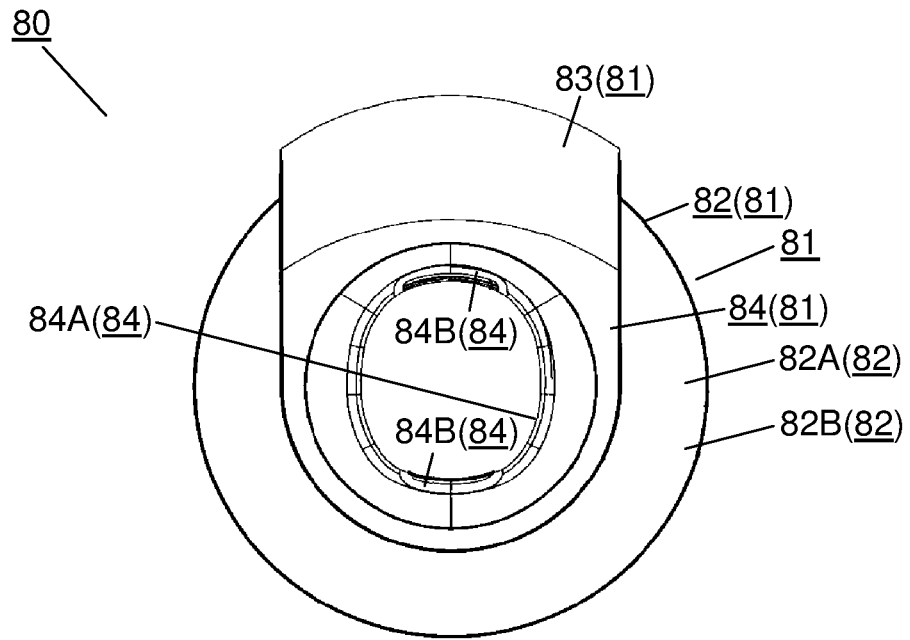
FIG. 12 is a plan view of the charging stand in FIG. 1.

Base 82 is formed in a substantially circular shape (including a circular shape) in a plan view, viewed from above, shown in FIG. 12.

Figure 11:
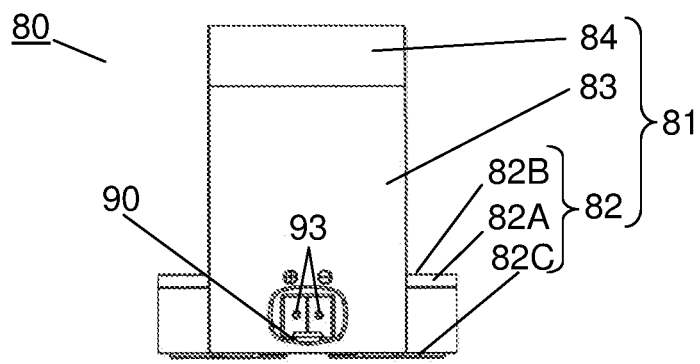
FIG. 11 is a rear view of the charging stand in FIG. 1.
Figure 13:
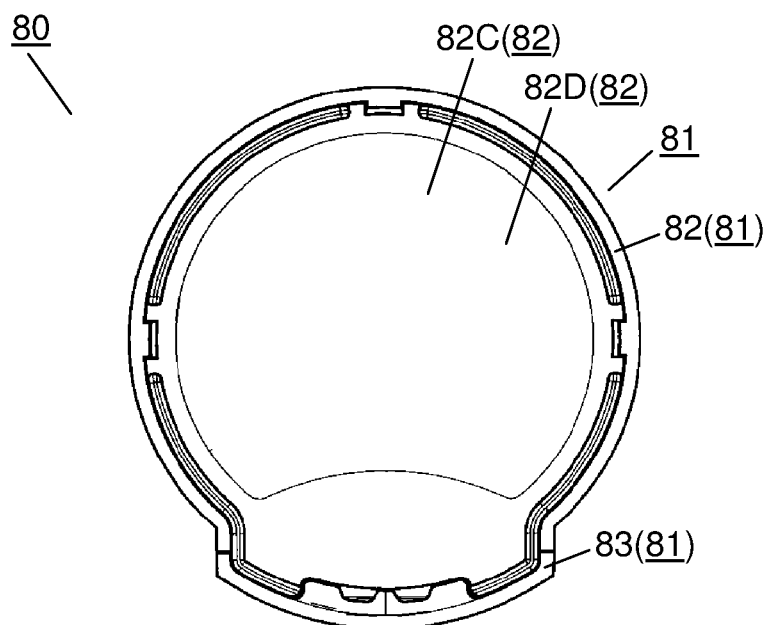
FIG. 13 is a bottom view of the charging stand in FIG. 1.

Base 82 includes top plate 82A and bottom plate 82C as shown in FIG. 11. Top surface 82B configured of top plate 82A of base 82 has a flat shape, for example. Therefore, the user can easily wipe out stain from top surface 82B. Top plate 82A may be configured to be detachable from base 82. In this case, the user can take out top plate 82A and easily wash top plate 82A with water. Further, as shown in FIG. 13, bottom surface 82D configured of bottom plate 82C of base 82 has a flat shape, for example. Therefore, base 82 can be stably kept stood, against fall in various directions, in a state that charging stand 80 itself or electric toothbrush 10 is mounted.

Support part 84 has hole 84A formed to extend in a height direction (a direction orthogonal to a paper surface), as shown in FIG. 12. That is, support part 84 has hole 84A in an approximately ring shape (including a ring shape) into which body 20 (refer to FIG. 1) of electric toothbrush 10 can be inserted. Hole 84A is formed in an elliptical shape in a plan view, viewed from above, shown in FIG. 12. In this case, as shown in FIG. 14, the top surface of support part 84 and the inner peripheral surface of hole 84A are integrally formed. Therefore, as compared with a case of forming the top surface of support part 84 and the inner peripheral surface of hole 84A by combining separate members, support part 84 can be structured such that a liquid such as water cannot easily enter the inside of support part 84.

Further, the elliptical shape of hole 84A is formed in a shape similar to a shape of the elliptical shape of grip part 22, as shown in FIG. 19. An inner diameter of hole 84A is formed slightly larger than an outer diameter of supported part 23 out of grip part 22 of body 20. Therefore, supported part 23 of grip part 22 can be easily inserted into hole 84A. Hole 84A and supported part 23 have cross sections in elliptical shapes as described above. Therefore, when supported part 23 is inserted into hole 84A, rotation of body 20 is prevented.

Further, an opening on an upper side of hole 84A is formed in a curved surface shape such that an inner diameter of hole 84A expands toward an upper direction, as shown in FIG. 14. Therefore, in the case of inserting body 20 (refer to FIG. 18) into hole 84A from above, bottom surface 27A of body 20 is easily guided to an inner side (downward) along the opening of hole 84A.

Figure 18:
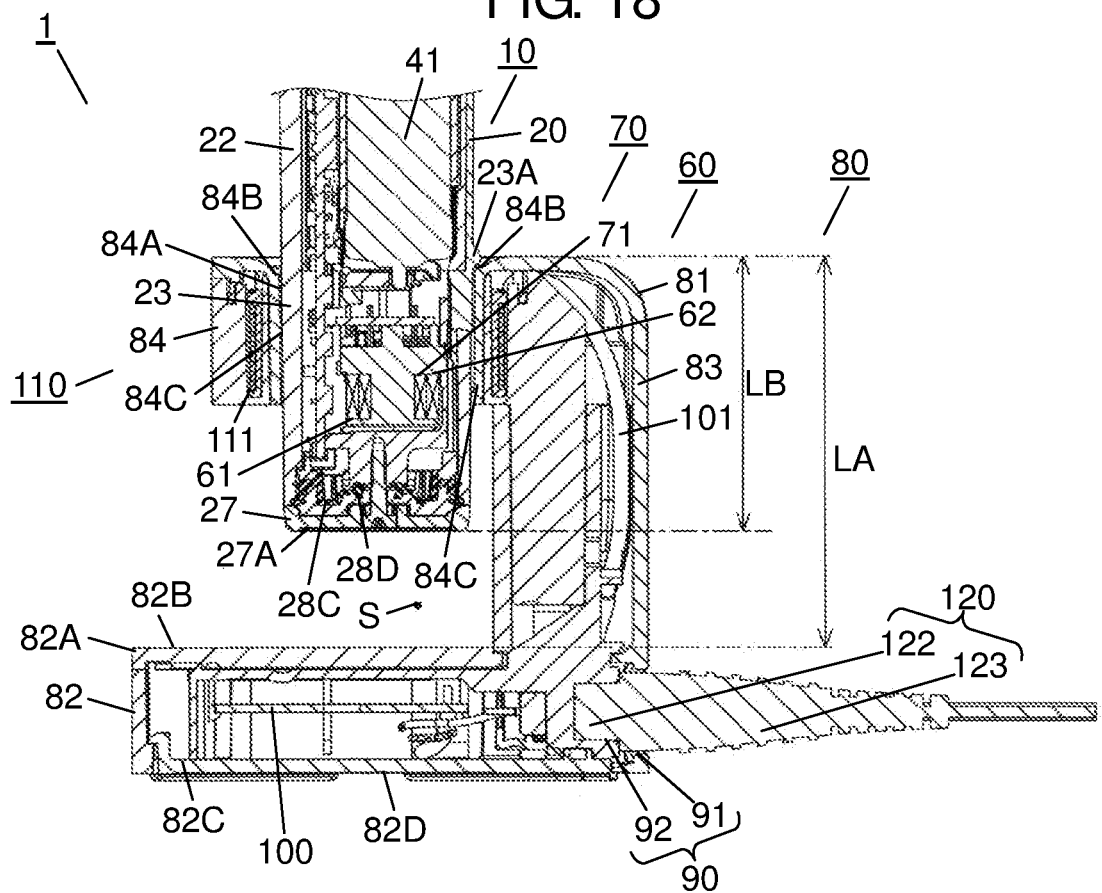
FIG. 18 is a cross-sectional view taken along line 18-18 in FIG. 2.

Further, hole 84A includes two recesses 84B on an edge of an upper side opening, as shown in FIG. 12. An upper surface of recess 84B has a planar shape in the direction orthogonal to the height direction. Therefore, when body 20 is inserted into hole 84A, protrusion 23A of body 20 is caught in recess 84B of hole 84A, as shown in FIG. 18, and no more insertion is stopped. In the above state, distance LA from recess 84B to top surface 82B of base 82 is larger than distance LB from protrusion 23A to bottom surface 27A which is formed of lower cap 27 of body 20. That is, when body 20 is inserted into hole 84A, gap S (LA-LB) is formed between bottom surface 27A of body 20 and top surface 82B of base 82 As a result, body 20 of electric toothbrush 10 is supported on charging stand 80 in a state that bottom surface 27A is floated from top surface 82B of base 82. Gap S is preferably about 1 mm to 30 mm, and more preferably, about 16 mm, for example.

Two recesses 84B, for example, are formed in the opening of hole 84A. As described above, hole 84A is formed in an elliptical shape. Therefore, body 20 can be inserted into hole 84A at a position of 180 degrees different in a peripheral direction with respect to charging stand 80. Accordingly, the user can optionally select, at time of inserting body 20, to which one of the two recesses 84B, protrusion 23A of body 20 should be hooked.

Hole 84A of support part 84 includes two guide parts 84C protruding toward a center axis of hole 84A, on an inner periphery, as shown in FIG. 14. Two guide parts 84C are provided at opposite (facing) positions with the center axis of hole 84A interposed therebetween. Further, two guide parts 84C are formed at mutually different positions in an axial direction (a height direction) of hole 84A. Therefore, body 20 of electric toothbrush 10 is inserted into hole 84A while two guide parts 84C maintain a posture of body 20 such that a height direction of body 20 is parallel to an axial direction of hole 84A.

Figure 15:
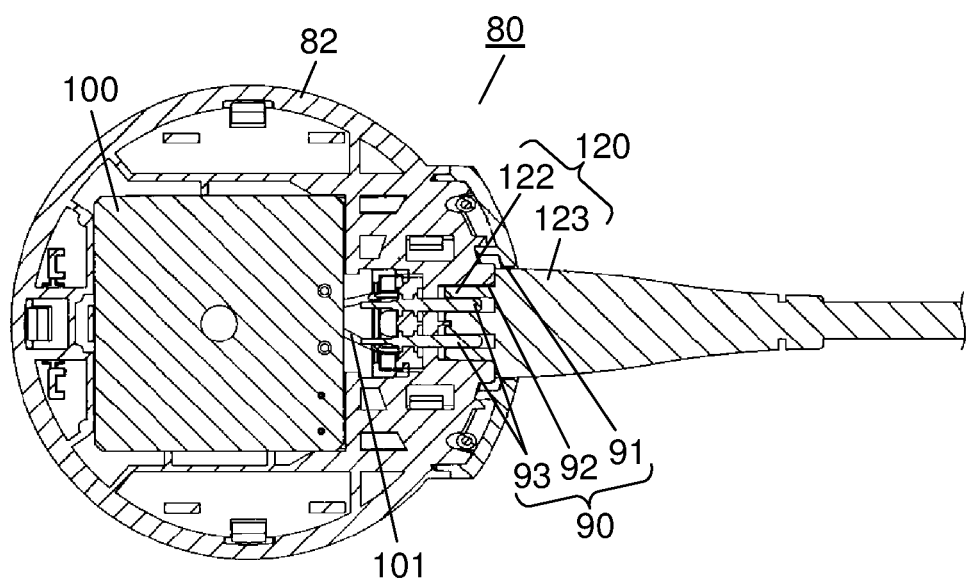
FIG. 15 is a cross-sectional view taken along line 15-15 in FIG. 10.

Connection part 90 of charging stand 80 is provided on an opposite side of base 82, on a lower side of pillar 83, as shown in FIG. 15. Connection part 90 is formed in a recess shape inward from an outer peripheral side surface of pillar 83, for example. Connection part 90 includes, inside, terminal 93 connected to a terminal (not shown) of power source line 120. Via terminal 93, power is supplied from power source line 120, and supplied power is supplied to power transmission device 110.

Connection part 90 has a stepped structure as a waterproof structure. Specifically, the stepped structure of connection part 90 includes large diameter part 91 on a surface side of case 81, and small diameter part 92 on a back side of large diameter part 91. On the other hand, power source line 120 includes small diameter part 122 on a front end side to be inserted into connection part 90, and large diameter part 123 which is continuous with small diameter part 122. Therefore, when power source line 120 is connected to connection part 90, small diameter part 122 of power source line 120 is inserted into small diameter part 92 of connection part 90. Similarly, large diameter part 123 of power source line 120 is inserted into large diameter part 91 of connection part 90. In this case, connection part 90 is formed such that a gap between large diameter part 123 and large diameter part 91 (for example, 0 mm to 0.4 mm) is smaller than a gap between small diameter part 122 and small diameter part 92 (for example, 1 mm or more). Therefore, water entering from an outside to the inside of connection part 90 remains in large diameter part 91 of connection part 90 more easily than in small diameter part 122 of power source line 120, by a capillary phenomenon. Accordingly, adhesion of water entering connection part 90 to terminal 93 can be prevented. As a result, reliability in connection part 90 can be maintained for a long time.

Substrate 100 of charging stand 80 is provided inside base 82, as shown in FIG. 14.

Figure 16:
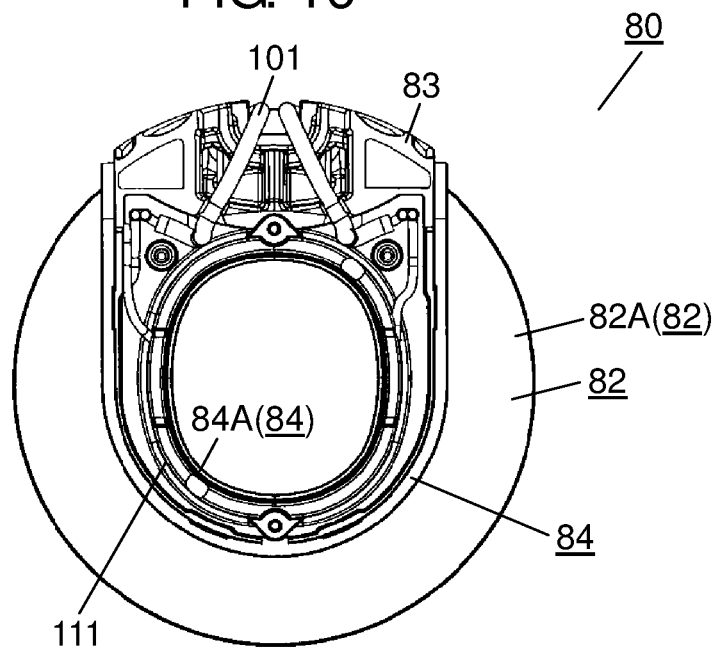
FIG. 16 is a plan view of the charging stand from which a top surface of a support part in FIG. 9 is removed.
Figure 17:
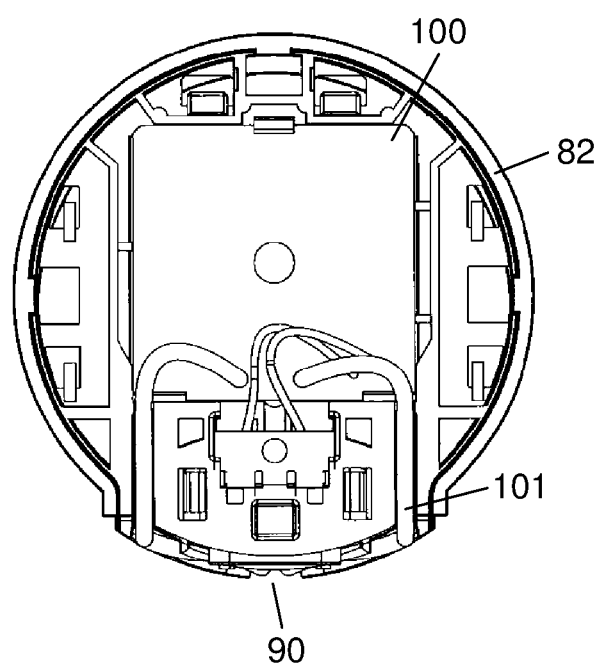
FIG. 17 is a bottom view of the charging stand from which a bottom plate of a base in FIG. 9 is removed.

Power transmitting coil 111 is provided inside support part 84, as shown in FIG. 16. Power transmitting coil 111 configures a primary-power supply part of power transmission device 110. An element configuring the circuit of substrate 100 and power transmitting coil 111 are electrically connected by lead wire 101 disposed through an inside of pillar 83, as shown in FIG. 17.

Next, a disposition relationship between power transmitting coil 111 and power receiving unit 61 disposed in charging stand 80 will be described with reference to FIG. 20.

Figure 20:
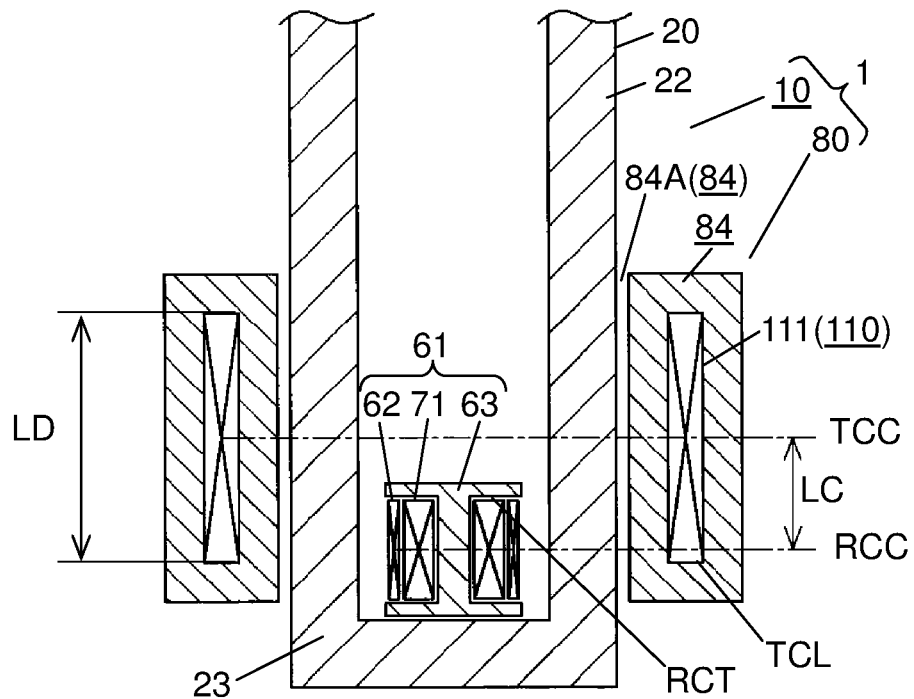
FIG. 20 is a schematic view showing a disposition relationship between a power transmitting coil and a power receiving unit in FIG. 18.

As shown in FIG. 20, in a state that body 20 is supported by charging stand 80, center TCC of power transmitting coil 111 in an axial direction and center RCC of magnetism collecting coil 71 of power receiving unit 61 in an axial direction are disposed in a shifted manner. Specifically, in the axial direction, center RCC of magnetism collecting coil 71 is positioned below center TCC of power transmitting coil 111. Further, upper end RCT of magnetism collecting coil 71 is positioned above lower end TCL of power transmitting coil 111. Accordingly, in the axial direction, at least a part of magnetism collecting coil 71 and at least a part of power transmitting coil 111 are disposed in an overlapping manner. In this case, distance LC between center TCC of power transmitting coil 111 and center RCC of magnetism collecting coil 71 of power receiving unit 61 is preferably less than a half of length LD of power transmitting coil 111 in the axial direction. This is because when distance LC exceeds a half of length LD, coupling of the power transmitting coil and the magnetism collecting coil becomes too small.

As described above, charging stand 80 of noncontact power supply device 1 of the present exemplary embodiment is configured.

Hereinafter, a circuit configuration of power transmission device 110 for noncontact power supply device 1 according to the present exemplary embodiment will be described in detail with reference to FIG. 21.

Figure 21:
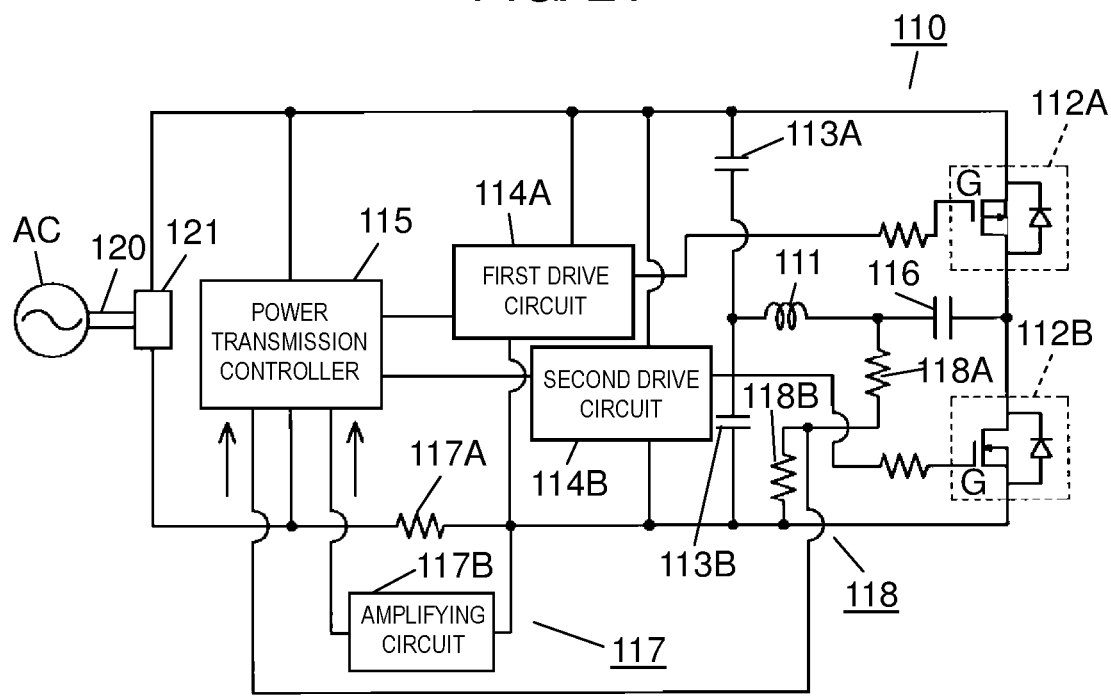
FIG. 21 is a block diagram of the power transmission device for the noncontact power supply device in FIG. 1.

Power transmission device 110 of charging stand 80 is connected to alternating-current power source AC through power source line 120 and connection part 90, as shown in FIG. 21. Power source line 120 includes power source circuit 121 for converting alternating-current power of alternating-current power source AC into direct-current power.

Power transmission device 110 includes power transmitting coil 111, and first switching element 112A, second switching element 112B, capacitors 113A, 113B, first drive circuit 114A, second drive circuit 114B, power transmission controller 115, power-transmission resonant capacitor 116, current detecting circuit 117, and voltage detecting circuit 118 that are mounted on substrate 100.

First switching element 112A and second switching element 112B convert direct current (power) obtained by conversion in power source circuit 121, into alternating power by switching operation of ON/OFF. The alternating power obtained by conversion is supplied to power transmitting coil 111. In this case, power source circuit 121 functions as a constant-voltage power source of 5 V, for example.

First switching element 112A and second switching element 112B are connected in series. First switching element 112A and second switching element 112B are configured of field-effect transistors (FET), for example. Specifically, first switching element 112A is configured of a P-channel FET, and second switching element 112B is configured of an N-channel FET. Then, a half-bridge circuit is configured of first switching element 112A and second switching element 112B. Further, first switching element 112A is connected to capacitor 113A, and second switching element 112B is connected to capacitor 113B. Capacitors 113A and 113B have the same capacitances, and divide a direct-current voltage applied to the half-bridge circuit into about a half (½).

First switching element 112A is connected to first drive circuit 114A. Second switching element 112B is connected to second drive circuit 114B.

Power transmission controller 115 controls power supplied from first drive circuit 114A to first switching element 112A, and from second drive circuit 114B to second switching element 112B. Power transmission controller 115 outputs a command signal of PWM (Pulse Width Modulation) to first drive circuit 114A and second drive circuit 114B, for example. First drive circuit 114A and second drive circuit 114B supply power based on an input PWM signal to first switching element 112A and second switching element 112B. Each of first switching element 112A and second switching element 112B generates alternating power to be supplied to power-transmission resonant capacitor 116, by repeating a switching operation of ON/OFF.

Power-transmission resonant capacitor 116 is disposed to be connected in series between a connecting point of first switching element 112A and second switching element 112B, and power transmitting coil 111. Power-transmission resonant capacitor 116 and power transmitting coil 111 configure a power-transmission resonant circuit. In this case, a power-transmission resonance frequency of power-transmission resonant capacitor 116 and power transmitting coil 111 configuring a power-transmission resonant circuit is set to become smaller than the drive frequency for driving first switching element 112A and second switching element 112B.

Current detecting circuit 117 includes resistor 117A and amplifying circuit 117B. Resistor 117A is connected to a ground side of power transmission device 110, and is used for detecting an input current input to power transmission device 110. Amplifying circuit 117B amplifies a voltage generated on both ends of resistor 117A. Amplifying circuit 117B converts a magnitude of a current detected by resistor 117A into a voltage, amplifies the voltage, and outputs the voltage to power transmission controller 115.

Voltage detecting circuit 118 is connected to a connecting point between power-transmission resonant capacitor 116 and power transmitting coil 111, and is connected to a ground side via two resistors 118A, 118B. Voltage detecting circuit 118 detects a resonance voltage V as a voltage of the power-transmission resonant circuit. Voltage detecting circuit 118 outputs resonance voltage V detected at a connecting point between two resistors 118A, 118B, to power transmission controller 115. Power transmission controller 115 controls a transmission mode and a standby mode described later, by switching between the modes, based on resonance voltage V. That is, when resonance voltage V is lower than a predetermined voltage, power transmission controller 115 determines that body 20 shown in FIG. 18 is supported on charging stand 80 and sets the mode to the transmission mode. On the other hand, when resonance voltage V is at or higher than the predetermined voltage, power transmission controller 115 determines that body 20 is not supported on charging stand 80 and sets the mode to the standby mode. In the standby mode, less power than that in the transmission mode is supplied to power transmitting coil 111 of power transmission device 110.

As described above, the circuit of power transmission device 110 for noncontact power supply device 1 is configured.

Hereinafter, a circuit configuration of magnetism collecting device 70 and power reception device 60 for noncontact power supply device 1 will be described with reference to FIG. 22.

Figure 22:
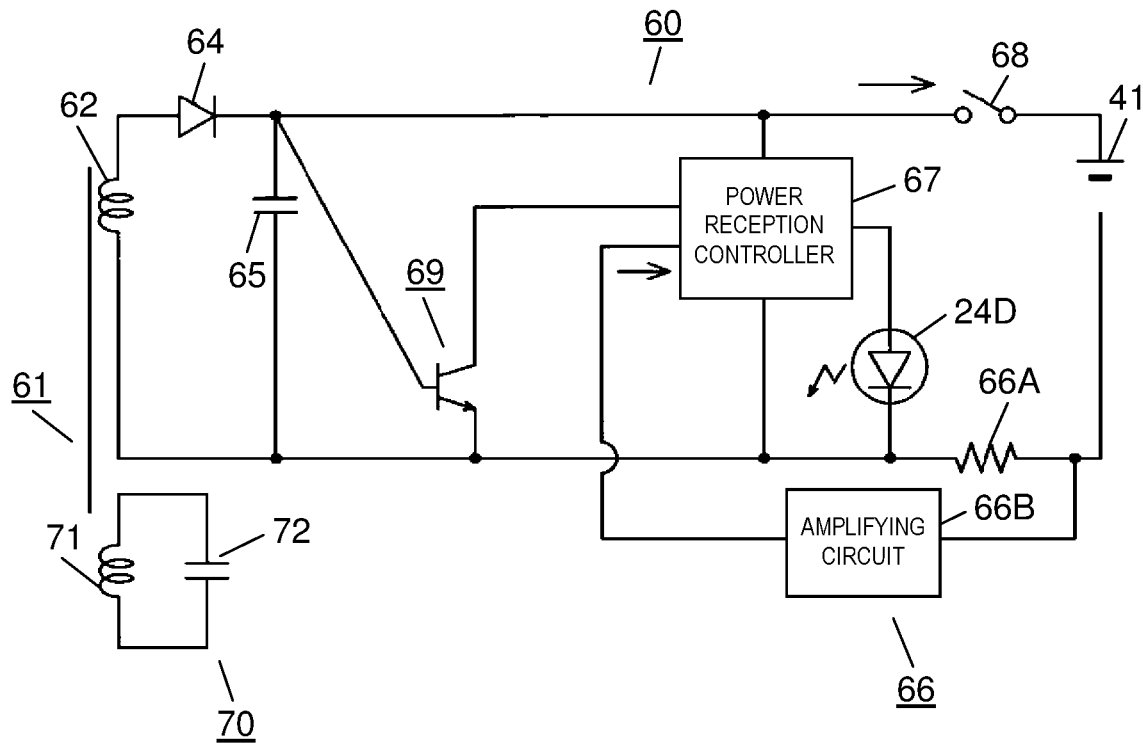
FIG. 22 is a block diagram of a magnetism collecting device and the power reception device for the noncontact power supply device in FIG. 1.

Magnetism collecting device 70 of electric toothbrush 10 includes magnetism collecting coil 71 and magnetism-collecting resonant capacitor 72, as shown in FIG. 22. Magnetism collecting coil 71 and magnetism-collecting resonant capacitor 72 form a magnetism collecting circuit that configures the magnetism-collecting resonant circuit. Further, magnetism-collecting resonant capacitor 72 is mounted on substrate 50 (refer to FIG. 6).

Power reception device 60 of electric toothbrush 10 includes power receiving coil 62 that is magnetically coupled with magnetism collecting coil 71, diode 64 and smoothing capacitor 65 that configure a rectifier circuit, current detecting circuit 66, power reception controller 67, switch 68, timing detecting circuit 69, and charge display unit 24D. Diode 64, smoothing capacitor 65, current detecting circuit 66, power reception controller 67, switch 68, and timing detecting circuit 69 are mounted on substrate 50, and are connected to rechargeable battery 41 which is a load. Accordingly, magnetism collecting device 70 and power reception device 60 are not electrically connected, and are magnetically coupled. Therefore, magnetism collecting device 70 is not connected to rechargeable battery 41 which is a load.

Next, operation and advantageous effects of power reception device 60 and magnetism collecting device 70 will be described.

First, in the transmission mode, the alternating magnetic flux generated from power transmitting coil 111 shown in FIG. 21 interlinks with magnetism collecting coil 71 shown in FIG. 20. Then, by magnetic resonance of power transmission device 110 and magnetism collecting device 70, power is transmitted from power transmitting coil 111 to magnetism collecting coil 71. Power transmitted to magnetism collecting coil 71 is transmitted from magnetism collecting coil 71 to power receiving coil 62, based on electromagnetic induction by power reception device 60 and magnetism collecting device 70. Accordingly, alternating power is generated in power receiving coil 62. That is, power transmitting coil 111 of power transmission device 110 (refer to FIG. 6) transmits power to power receiving coil 62 of power reception device 60, via magnetism collecting coil 71 of magnetism collecting device 70. That is, power receiving unit 61 including power transmitting coil 111, power receiving coil 62, and magnetism collecting coil 71 configures a noncontact power transmitting unit. The alternating power generated in power receiving coil 62 of power receiving unit 61 is converted from an alternating current to a direct current by diode 64. Diode 64 is connected to smoothing capacitor 65, and rechargeable battery 41 which is a load. Smoothing capacitor 65 reduces noise contained in the direct current obtained by conversion by diode 64. Rechargeable battery 41 is supplied with the direct current obtained by conversion by diode 64. Between diode 64 and rechargeable battery 41, there is disposed switch 68 for turning ON/OFF the supply of the converted direct current.

Current detecting circuit 66 of power reception device 60 includes resistor 66A and amplifying circuit 66B. Resistor 66A is connected to a ground side of power reception device 60, and is used for detecting an input current input to rechargeable battery 41 which is a load. Amplifying circuit 66B amplifies a voltage generated on both ends of resistor 66A. Amplifying circuit 66B converts a magnitude of a current detected by resistor 66A into a voltage, amplifies the voltage, and outputs the voltage to power reception controller 67.

Power reception controller 67 controls a charge operation of rechargeable battery 41, by switching the ON/OFF of switch 68, based on a voltage detected by current detecting circuit 66. That is, power reception controller 67 switches the operation between supply and non-supply of power to rechargeable battery 41. Specifically, when the voltage of rechargeable battery 41 is less than a predetermined voltage (3 V, in the case of a lithium ion battery, for example), power reception controller 67 switches switch 68 to ON, and starts charging. On the other hand, when the voltage of rechargeable battery 41 is equal to or greater than a predetermined voltage (4.2 V, in the case of a lithium ion battery, for example), power reception controller 67 switches switch 68 to OFF, and stops charging.

Power reception controller 67 switches the display of charge display unit 24D. Specifically, power reception controller 67 turns on charge display unit 24D when charge to rechargeable battery 41 is being performed. On the other hand, when charge to rechargeable battery 41 is not being performed, charge display unit 24D is not turned on. Accordingly, this can make the user recognize whether charging is being performed.

Furthermore, by switching between ON and OFF of switch 68, power reception controller 67 communicates with power transmission controller 115 of power transmission device 110 (refer to FIG. 21), and detects body 20. Power transmission controller 115 detects with voltage detecting circuit 118 (refer to FIG. 21), resonance voltage V which varies by switching switch 68 of power reception device 60. Accordingly, power transmission controller 115 adjusts the output of the alternating power generated by power transmitting coil 111.

Timing detecting circuit 69 of power reception device 60 shown in FIG. 22 detects presence or absence of a waveform, in a predetermined period, of alternating power generated by power receiving coil 62. The waveform detected by timing detecting circuit 69 correlates with the output of alternating power supplied to power transmitting coil 111 of power transmission device 110 (refer to FIG. 21). Therefore, timing detecting circuit 69 can detect presence or absence of alternating power supplied to power transmitting coil 111. Timing detecting circuit 69 is configured of a transistor, for example.

Hereinafter, a detailed operation of timing detecting circuit 69 will be described.

First, when alternating power is generated in power receiving coil 62, a voltage is continuously applied to power receiving coil 62. Therefore, a transistor configuring timing detecting circuit 69 continues in a state of ON. In this case, timing detecting circuit 69 outputs first timing signal SA to power reception controller 67. On the other hand, when alternating power is not generated in power receiving coil 62, the transistor becomes in a state of OFF. In this case, timing detecting circuit 69 outputs second timing signal SB to power reception controller 67. That is, power reception controller 67, based on first timing signal SA or second timing signal SB that is input, detects presence or absence of alternating power supplied from power transmission device 110. Power reception controller 67 performs control of ON/OFF operation of switch 68 and control of a lighting operation of charge display unit 24D.

Next, switch control of the ON/OFF operation of first switching element 112A and second switching element 112B, the switch control being performed by power transmission controller 115 of power transmission device 110 will be described with reference to FIG. 21 and FIG. 23.

Figure 23:
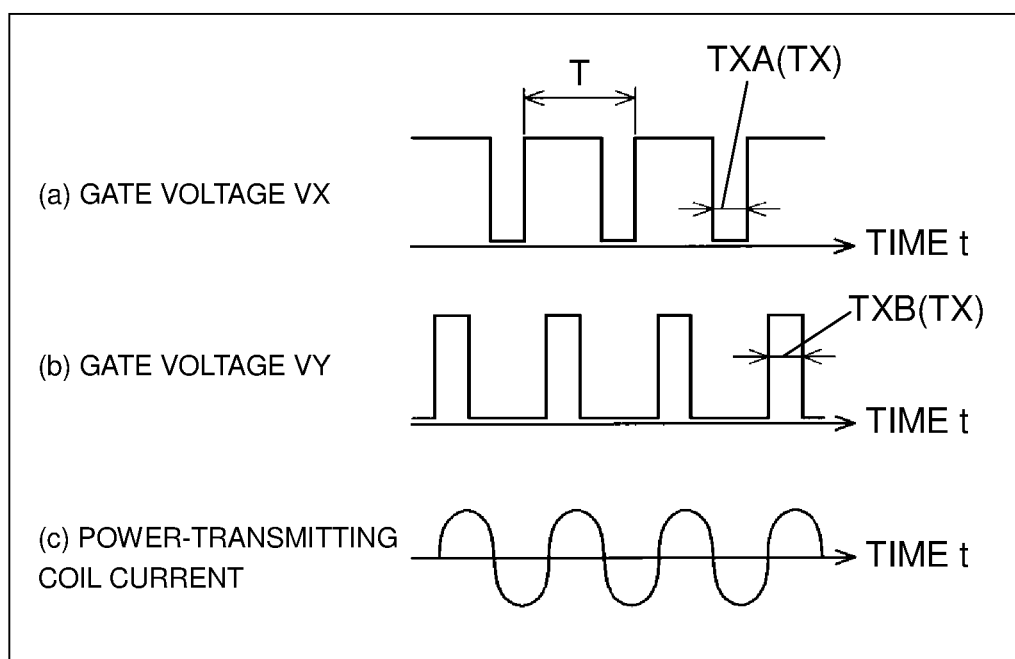
FIG. 23 is a timing chart showing a first example of control of the switching elements which is performed by the power transmission controller in FIG. 21.

Power transmission controller 115 outputs from first drive circuit 114A, a PWM signal for causing gate G of first switching element 112A to repeat the ON/OFF operation, as shown in (a) in FIG. 23. The PWM signal includes information of first ON time TXA corresponding to ON time TX in the operation of one cycle T (for example, 7 μs) as a length for keeping first switching element 112A ON. In this case, as described above, first switching element 112A is configured of a P-channel FET. Therefore, first switching element 112A becomes in an ON state, when gate voltage VX of a low level (for example, 0 V) is applied to gate G. On the other hand, first switching element 112A becomes in an OFF state, when gate voltage VX of a high level (for example, 5 V as an input voltage from power source circuit 121) is applied to gate G.

Further, power transmission controller 115 outputs from second drive circuit 114B, a PWM signal for causing gate G of second switching element 112B to repeat the ON/OFF operation, as shown in (b) in FIG. 23. The PWM signal includes information of second ON time TXB corresponding to ON time TX in the operation of one cycle T (for example, 7 μs) as a length for keeping second switching element 112B ON. In this case, as described above, second switching element 112B is configured of an N-channel FET. Therefore, second switching element 112B becomes in an OFF state, when gate voltage VY of a low level is applied to gate G. On the other hand, second switching element 112B becomes in an ON state, when gate voltage VY of a high level is applied to gate G.

Power transmission controller 115 outputs a PWM signal to gates G of first switching element 112A and second switching element 112B such that first ON time TXA in which first switching element 112A becomes ON and second ON time TXB in which second switching element 112B becomes ON are alternate in time sequence. Accordingly, as shown in (c) in FIG. 23, a power-transmitting coil current flowing through power transmitting coil 111 of power transmission device 110 becomes in a sinusoidal waveform, for example.

In this case, as described above, a relationship between power-transmission resonance frequency f1, drive frequency fD, and power-reception resonance frequency f2 is set to satisfy f1<fD<f2. Power-transmission resonance frequency f1 is a resonance frequency of a power-transmission resonant circuit. Drive frequency fD is the frequency of the PWM signal applied to gates G of first switching element 112A and second switching element 112B. Power-reception resonance frequency f2 is a resonance frequency of a magnetism collecting circuit itself or a power reception device including a magnetism collecting circuit.

The relationship of f1<fD<f2 is realized by the following set of conditions.

First, a value of each configuration element is set in a state that body 20 is supported by charging stand 80 as shown in FIG. 1, and power receiving unit 61 and power transmitting coil 111 are disposed as shown in FIG. 18.

Specifically, the design value of inductance L of power transmitting coil 111 is set to 4 µH. A design value of capacitance C of power-transmission resonant capacitor 116 is set to 0.36 µF. A design value of inductance L of magnetism collecting coil 71 is set to 14 µH. A design value of capacitance C of magnetism-collecting resonant capacitor 72 is set to 77200 pF. A design value of inductance L of power receiving coil 62 is set to 2 µH.

In this case, power-transmission resonance frequency f1 and power-reception resonance frequency f2 are calculated in accordance with Equation (1).

$$f=1/(2\pi\sqrt{LC}) \quad (1)$$

That is, when each resonant circuit is designed in the above design value, power-transmission resonance frequency f1 becomes about 133 kHz, and power-reception resonance frequency f2 becomes about 153 kHz.

Then, drive frequency fD is set to 143 kHz, for example, so as to satisfy the relationship of f1<fD<f2, based on designed power-transmission resonance frequency f1 and power-reception resonance frequency f2.

However, as described above, drive frequency fD may vary from the design value due to an influence of an oscillator which is a component. For example, in the case of setting drive frequency fD to 143 kHz, when a variation of ±0.5% from the design value occurs, drive frequency fD varies in a range of about 142 kHz to 144 kHz.

Further, when power transmitting coil 111 and magnetism collecting coil 71 vary by ±5% from a design value and power-transmission resonant capacitor 116 and magnetism-collecting resonant capacitor 72 vary by ±5% from a design value, power-transmission resonance frequency f1 and power-reception resonance frequency f2 become as follows. That is, due to the variation in the components, power-transmission resonance frequency f1 can be in a range of 126 kHz to 140 kHz, and power-reception resonance frequency f2 can be in a range of 145 kHz to 162 kHz.

Therefore, in noncontact power supply device 1 according to the present exemplary embodiment, the design values of the components are set such that the relationship of f1<fD<f2 is maintained even when a variation in a general magnitude (for example, about ±5%) occurs in the components, for example.

On the other hand, in a state that main body 20 is not supported by charging stand 80, inductance L of power transmitting coil 111 becomes as follows.

In this case, magnetic core 63 configuring power receiving unit 61 is not present near power transmitting coil 111. Therefore, inductance L of power transmitting coil 111 becomes smaller than that when power receiving unit 61 shown in FIG. 18 is positioned near power transmitting coil 111.

That is, a value of inductance L of power transmitting coil 111 changes between a case of disposition when magnetic core 63 is present near power transmitting coil 111 shown in FIG. 18 and a case of disposition when magnetic core 63 is not present. Therefore, in the present exemplary embodiment, regardless of presence or absence of magnetic core 63, an arrangement position and magnetic core 63 are designed such that power-transmission resonance frequency f3 is set to a frequency that is equal to or less than drive frequency fD. Power-transmission resonance frequency f3 is a value corresponding to power-transmission resonance frequency f1 of the power-transmission resonant circuit when magnetic core 63 is not present.

Specifically, the arrangement position and magnetic core 63 are designed such that a change in inductance L when magnetic core 63 is not near power transmitting coil 111 falls within −3%, for example. In this case, inductance L of power transmitting coil 111 in a state in which body 20 is not supported by charging stand 80 is in a range of 3.7 µH to 4.1 µH. Accordingly, power-transmission resonance frequency f3 varies within a range of 128.3 kHz to 141.8 kHz from Equation (1). In this case, the relationship of f3<fD is also satisfied.

That is, power-transmission resonance frequency f1 when the coupling coefficient of power transmitting coil 111 and magnetism collecting coil 71 is included in a first range, and power-transmission resonance frequency f3 when the coupling coefficient of power transmitting coil 111 and magnetism collecting coil 71 is included in a second range smaller than the first range and when body is not disposed in power transmission device, can be set to a frequency smaller than drive frequency fD. The first range is a coupling coefficient of power transmitting coil 111 and magnetism collecting coil 71 in a state that body 20 shown in FIG. 1 is supported by charging stand 80 and power receiving unit 61 and power transmitting coil 111 shown in FIG. 18 are disposed. On the other hand, the second range is a coupling coefficient of power transmitting coil 111 and magnetism collecting coil 71 when body 20 is disposed apart from charging stand 80.

Further, in the present exemplary embodiment, the design value of each component is set such that power-transmission resonance frequency f1 (f3) and power-reception resonance frequency f2 become values near drive frequency fD. Specifically, power-transmission resonance frequency f1 based on the design value is set to a frequency that is smaller (less) than drive frequency fD and equal to or higher than 85% of drive frequency fD. Similarly, power-reception resonance frequency f2 based on the design value is set to a frequency that is larger than (exceeds) drive frequency fD and equal to or less than 115% of drive frequency fD. When the value of power-reception resonance frequency f2 exceeds 85% and is less than 115%, required output and efficiency are not satisfied. Therefore, it is preferable that power-reception resonance frequency f2 is set to fall within the above range.

Further, impedance Z of the resonant circuit of power transmission device 110 is obtained by Equation (2) below. The value of r1 represents a resistance value of power transmitting coil 111.

$$Z = wL - 1/wC + r1 \qquad (2)$$

Figure 24:
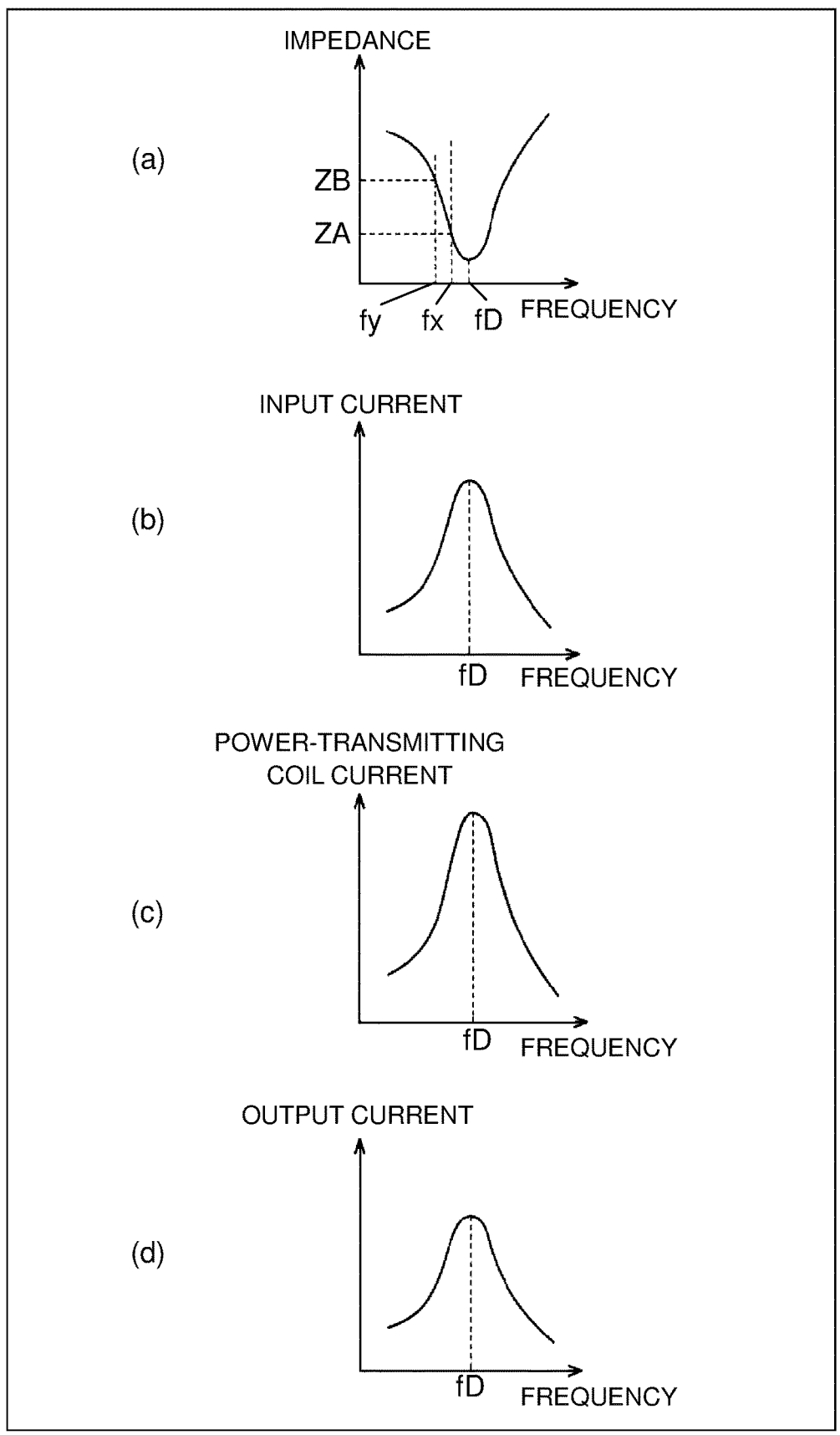
FIG. 24 is a graph showing a relationship between a current and a drive frequency of the noncontact power supply device in FIG. 1.

Usually, as shown in (b), (c), (d) of FIG. 24, when power-transmission resonance frequency f1 is closer to drive frequency fD, the input current of power transmission device 110, power-transmitting coil current flowing through power transmitting coil 111, and the output current of power transmission device 110 increase.

On the other hand, in the case where power-transmission resonance frequency f1 and power-reception resonance frequency f2 are close to drive frequency fD, when values of power transmitting coil 111, magnetism collecting coil 71, power-transmission resonant capacitor 116, and magnetism-collecting resonant capacitor 72 vary from the design values, impedance Z also varies from Equation (2). For example, as shown in (a) in FIG. 24, when power-transmission resonance frequency f1 is first power-transmission resonance frequency fx smaller than drive frequency fD, impedance Z shows first impedance ZA higher than when power-transmission resonance frequency f1 coincides with drive frequency fD. Further, when power-transmission resonance frequency f1 is smaller than first power-transmission resonance frequency fx and is second power-transmission resonance frequency fy farther from drive frequency fD, impedance Z shows second impedance ZB much higher than when power-transmission resonance frequency f1 coincides with drive frequency fD.

That is, when impedance Z varies, the power-transmitting coil current flowing through power transmitting coil 111 varies. Therefore, the input current and the output current also vary.

Accordingly, in the present exemplary embodiment, power transmission controller 115 of power transmission device 110 prevents variation in the power-transmitting coil current by the following method.

First, in response to power transmission device 110, power reception device 60, and magnetism collecting device 70, power transmission controller 115 measures in advance ON times TX, TY of a PWM signal applied to gates G of first switching element 112A and second switching element 112B. Then, measured ON times TX, TY are stored in a storage unit of power transmission controller 115. Specifically, in the above transmission mode, power transmission controller 115 sets ON time TX of first switching element 112A and second switching element 112B to first ON time TXA and second ON time TXB as first fixed values. On the other hand, in the above standby mode, power transmission controller 115 sets ON time TY of first switching element 112A and second switching element 112B to first ON time TYA and second ON time TYB as second fixed values. Then, in the transmission mode and the standby mode, power transmission controller 115 controls drive of first switching element 112A and second switching element 112B, based on the stored first fixed value and second fixed value. Accordingly, the variation in the power-transmitting coil current generated in power transmitting coil 111 of power transmission device 110 is prevented.

Hereinafter, a method of setting first ON times TXA, TYA and second ON times TXB, TYB of first switching element 112A and second switching element 112B will be described with reference to FIG. 21. ON time TX corresponds to the ON time in the above transmission mode. On the other hand, ON time TY corresponds to the ON time in the above standby mode.

First, a method of setting ON time TX in the transmission mode will be described.

First, elements configuring the circuit of power transmission device 110 are mounted on substrate 100. Then, in the state that power transmitting coil 111 is connected to power transmission device 110, the power source of which the output current is displayed and power transmission device 110 are connected.

Next, as shown in FIG. 18, body 20 is inserted into support part 84 of charging stand 80. Accordingly, power transmitting coil 111 of charging stand 80 and power receiving unit 61 of body 20 are disposed in a state of performing a charging operation. A prescribed voltage (for example, 5 V) is set to an external power source, and the voltage is applied to connection part 90 which is an input part of power transmission device 110. This disposition corresponds to a state of the transmission mode.

Next, the output of the PWM signal is changed, and is applied to the gates G of first switching element 112A and second switching element 112B. In this case, the output of the PWM signal is adjusted such that the output current (a charge current) supplied to power receiving unit 61 of body 20 measured with a multimeter falls within a predetermined range. In this case, the ON time of the PWM signal when the output current is included in a predetermined range is set as ON time TX. Then, set ON time TX is stored in a storage unit (not shown) of power transmission controller 115.

That is, the output of the PWM signal is changed for each of first drive circuit 114A and second drive circuit 114B, and ON time TX is measured individually.

Specifically, ON time TX of the PWM signal of first drive circuit 114A is measured by changing ON time TX. Then, in a specific PWM signal, ON time TX when the output current (a charge current) is included in a predetermined range is set as first ON time TXA. Similarly, second ON time TXB is set based on ON time TX of a PWM signal of second drive circuit 114B. Then, set first ON time TXA and second ON time TXB are stored as a first fixed value in a storage unit of power transmission controller 115. The first fixed value is an exemplification of a fixed value in the transmission mode.

The predetermined range is a range from a lower limit to an upper limit of a target output current (a charge current).

By the above method, ON time TX in the transmission mode is set.

Hereinafter, a method of setting ON time TY in the standby mode will be described.

First, body 20 shown in FIG. 18 is removed from charging stand 80. Power transmitting coil 111 of charging stand 80 and magnetism collecting coil 71 of body 20 are disposed such that a coupling coefficient becomes sufficiently sparse (for example, "0"). By this arrangement, a state of the standby mode is obtained.

Next, in the standby mode state, because body 20 is not present unlike the above transmission mode, the output pf the PWM signal is adjusted while monitoring the output current of the power source. Then, the ON time of the PWM signal when the output current is included in a predetermined range is set as ON time TY. Then, set ON time TY is stored in the storage unit, not shown, of power transmission controller 115. The predetermined range is a range of an output current value which is set such that power consumption sufficiently satisfies regulations.

That is, the output of the PWM signal is changed for each of first drive circuit 114A and second drive circuit 114B, and ON time TY is measured individually.

Specifically, ON time TY of the PWM signal of first drive circuit 114A is measured by changing ON time TY. Then, in a specific PWM signal, ON time TY when the output current is included in a predetermined range is set as first ON time TYA. Similarly, second ON time TYB is set based on ON time TY of a PWM signal of second drive circuit 114B. Then, set first ON time TYA and second ON time TYB are stored as second fixed values in the storage unit (not shown) of power transmission controller 115. The second fixed value is an exemplification of a fixed value in the standby mode.

By the above method, ON time TY in the standby mode is set.

Examples of first ON times TXA, TYA and second ON times TXB, TYB of first switching element 112A and second switching element 112B are shown in FIG. 25 to FIG. 29. FIG. 25 to FIG. 29 each show an example of the case where drive frequency fD is 143 kHz and one cycle T is 7 µs.

Figure 25:
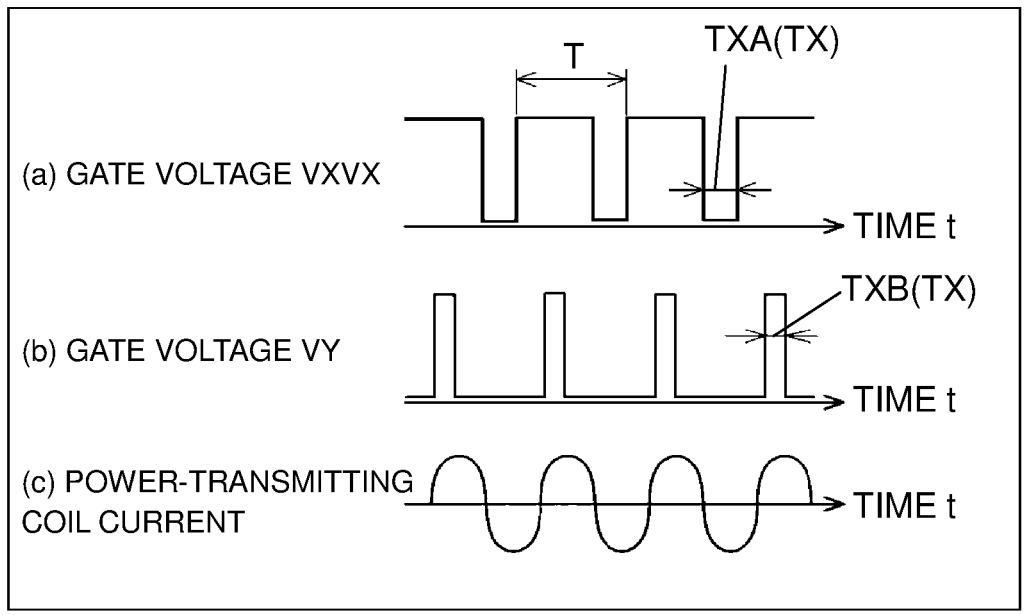
FIG. 25 is a timing chart showing a second example of control of the switching elements which is performed by the power transmission controller in FIG. 21.

Here, (a) and (b) in FIG. 25 show an example of a PWM signal when second ON time TXB is set smaller than first ON time TXA, in the transmission mode. In this case, first ON time TXA is set to 1 µs, and second ON time TXB is set to 0.75 µs. Accordingly, as shown in (c) in FIG. 25, the power-transmitting coil current flowing through power transmitting coil 111 of power transmission device 110 becomes in a sinusoidal waveform, for example.

Figure 26:
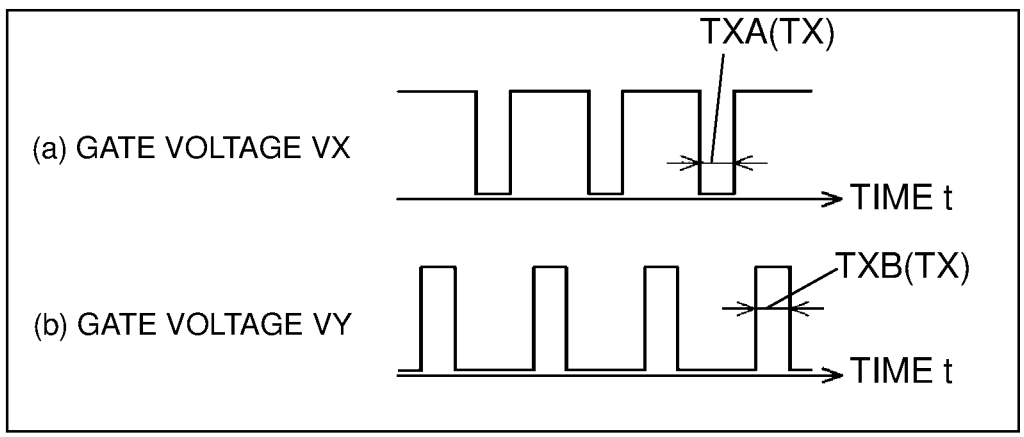
FIG. 26 is a timing chart showing a third example of control of the switching elements which is performed by the power transmission controller in FIG. 21.

Further, (a) and (b) in FIG. 26 show an example of setting of first ON time TXA and second ON time TXB in power transmission device 110 when impedance Z shown in (a) in FIG. 24 is second impedance ZB, in the transmission mode. In the case of second impedance ZB, first ON time TXA is set to 1 µs, and second ON time TXB is set to 1 µs.

Figure 27:
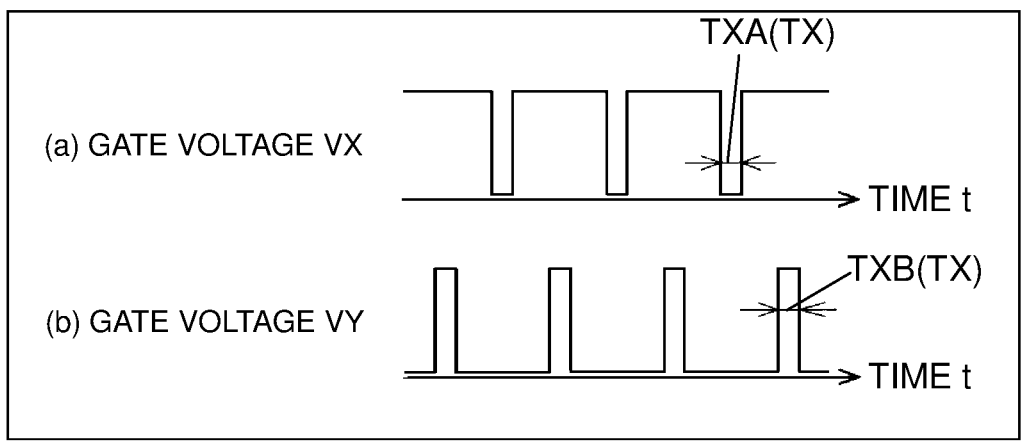
FIG. 27 is a timing chart showing a fourth example of control of the switching elements which is performed by the power transmission controller in FIG. 21.

Further, (a) and (b) in FIG. 27 show an example of setting of first ON time TXA and second ON time TXB in power transmission device 110 when impedance Z shown in (a) in FIG. 24 is first impedance ZA, in the transmission mode. In the case of first impedance ZA, first ON time TXA is set to 0.75 µs, and second ON time TXB is set to 0.75 µs.

As shown in FIG. 26 and FIG. 27, first ON time TXA and second ON time TXB of power transmission device 110 showing second impedance ZB are set in larger values than first ON time TXA and second ON time TXB of power transmission device 110 showing first impedance ZA.

Figure 28:
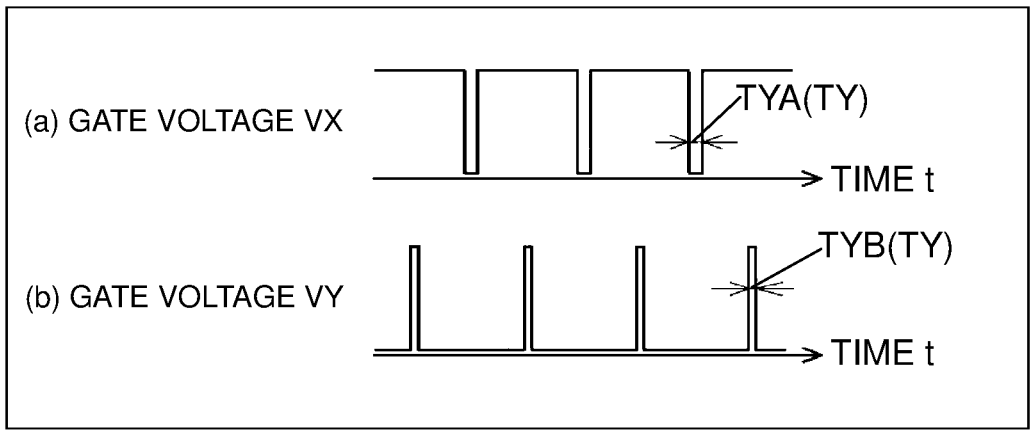
FIG. 28 is a timing chart showing a fifth example of control of the switching elements which is performed by the power transmission controller in FIG. 21.

Further, (a) and (b) in FIG. 28 show an example of setting of first ON time TYA and second ON time TYB in power transmission device 110 when impedance Z shown in (a) in FIG. 24 is second impedance ZB, in the standby mode. In the standby mode, in the case of second impedance ZB, first ON time TYA is set to 0.375 µs, and second ON time TYB is set to 0.125 µs. First ON time TXA and second ON time TXB shown in FIG. 26 are set in larger values than first ON time TYA and second ON time TYB shown in FIG. 28.

Figure 29:
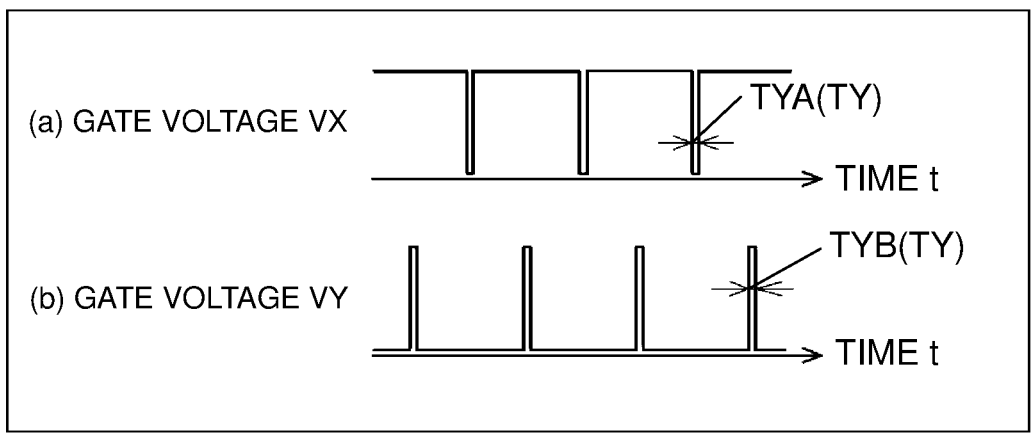
FIG. 29 is a timing chart showing a sixth example of control of the switching elements which is performed by the power transmission controller in FIG. 21.

Further, (a) and (b) in FIG. 29 show an example of setting of first ON time TYA and second ON time TYB in power transmission device 110 when impedance Z shown in (a) in FIG. 24 is first impedance ZA, in the standby mode. In the standby mode, in the case of first impedance ZA, first ON time TYA is set to 0.125 µs, and second ON time TYB is set to 0.125 µs. First ON time TXA and second ON time TXB shown in FIG. 27 are set in larger values than first ON time TYA and second ON time TYB shown in FIG. 29.

That is, from FIG. 26 and FIG. 28, and FIG. 27 and FIG. 29, when impedance Z is the same, ON time TX in the transmission mode is set in a larger value than ON time TY in the standby mode.

Example

Hereinafter, an example of noncontact power supply device 1 according to the present exemplary embodiment will be described with reference to FIG. 20 and FIG. 30.

First, design values of components configuring power transmitting coil 111 and power receiving unit 61 used in the example will be described.

Power transmitting coil 111 was formed of ten turns of a bundle of 140 wires, each wire having a 0.06 mm diameter. Further, power transmitting coil 111 was formed to have an axial length of 15 mm and an elliptical shape having a long side of 40 mm and a short side of 30 mm. Accordingly, power transmitting coil 111 was designed such that inductance L has a design value of 4 µH.

Magnetic core 63 of power receiving unit 61 was formed in a shape of an axial length of 9 mm and an outer diameter of 12 mm. In this case, an outer diameter of magnetic core 63 was configured to be substantially equal (including equal) to the outer diameter of power receiving unit 61.

Further, magnetism collecting coil 71 of power receiving unit 61 was formed of 16 turns of a bundle of 70 wires, each wire having a 0.06 mm diameter. Magnetism collecting coil 71 was formed in a shape of an axial length of 6 mm. Accordingly, magnetism collecting coil 71 was designed such that inductance L has a design value of 14 µH.

Power receiving coil 62 of power receiving unit 61 was formed of six turns of a wire of a 0.4 mm diameter. Power receiving coil 62 was formed in a shape of an axial length of 6 mm. Accordingly, power receiving coil 62 was designed such that inductance L has a design value of 2 µH.

Next, designed power transmitting coil 111 and power receiving unit 61 were disposed as shown in FIG. 20. The output current and the coupling coefficient were measured while changing distance LC. A result is shown in FIG. 30. Distance LC is an axial distance between center TCC of power transmitting coil 111 and center RCC of magnetism collecting coil 71 of power receiving unit 61 that have been described above.

Figure 30:
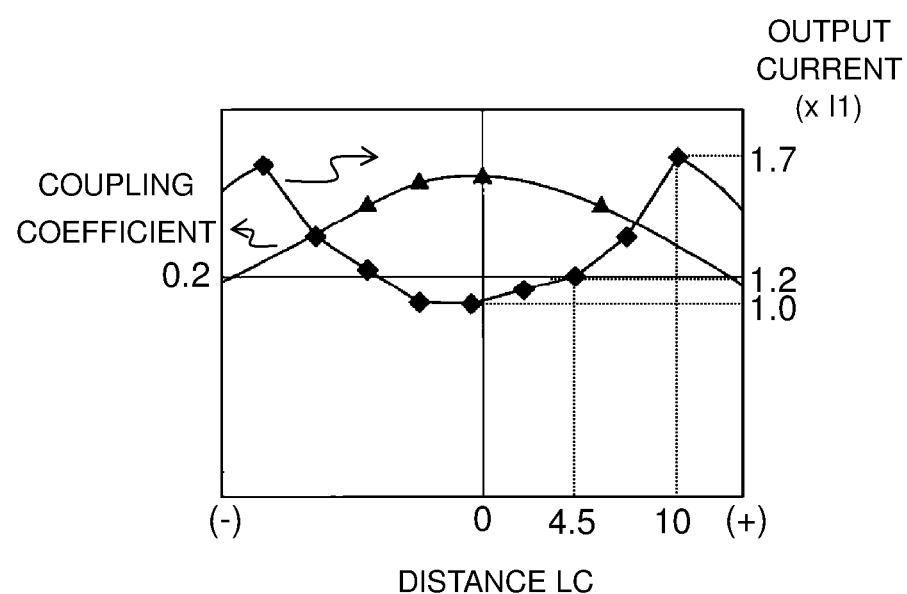
FIG. 30 is a graph showing a relationship between a coupling coefficient of a power transmitting coil and a magnetism collecting coil and an output current according to an example.

FIG. 30 shows an experimental result of the output current and the coupling coefficient obtained for distance LC, in noncontact power supply device 1 designed as described in the above exemplary embodiment.

As shown in FIG. 30, noncontact power supply device 1 according to the example has a largest coupling coefficient and a minimum output current, when distance LC is "0".

On the other hand, as the absolute value of distance LC increases, the output current flowing through power transmitting coil 111 increases. In this case, the output current becomes maximum in distance LC (for example, about 10 mm) when the coupling coefficient is near 0.2 and larger than 0.2. The output current decreases as the absolute value of distance LC becomes larger in distance LC when the coupling coefficient is near 0.2 and smaller than 0.2.

That is, it can be understood that, in the case of noncontact power supply device 1 according to the example, the output current when the absolute value of distance LC is 4.5 mm increases by about 20% (1.2×I1) more than the output current (for example, I1) when distance LC is 0 mm.

Based on a measurement result in FIG. 30, operation and advantageous effects of noncontact power supply device 1 will be described below with reference to FIG. 18.

First, as shown in FIG. 18, magnetism collecting coil 71 is disposed near a bottom part of body 20. When body 20 of electric toothbrush 10 is supported by charging stand 80, center TCC of power transmitting coil 111 in the axial direction and center RCC of magnetism collecting coil 71 in the axial direction are disposed in a shifted manner.

When center TCC of power transmitting coil 111 and center RCC of magnetism collecting coil 71 are shifted, the coupling coefficient of power transmitting coil 111 and magnetism collecting coil 71 becomes small, as shown in FIG. 30.

On the other hand, power transmitting coil 111 has an air-core, and magnetism collecting coil 71 is wound around magnetic core 63. In this case, in the axial direction of power transmitting coil 111, as center RCC of magnetism collecting coil 71 is shifted from center TCC of power transmitting coil 111, inductance L of power transmitting coil 111 decreases. Therefore, from Equation (1), power-transmission resonance frequency f1 of the power-transmission resonant circuit increases. According to the present exemplary embodiment, power-transmission resonance frequency f1 is designed to become smaller than drive frequency fD of first switching element 112A and second switching element 112B.

That is, as center RCC of magnetism collecting coil 71 is shifted from center TCC of power transmitting coil 111, power-transmission resonance frequency f1 approaches drive frequency fD. When power-transmission resonance frequency f1 and drive frequency fD are closer to each other, the input current increases as shown in (b) in FIG. 24. In this case, as shown in FIG. 30, when the absolute value of distance LC becomes larger (up to about 4.5 mm), the coupling coefficient of power transmitting coil 111 and magnetism collecting coil 71 becomes smaller, but the input current increases. As a result, the output current of power reception device 60 can be increased.

Further, magnetic core 63 according to the example is in a bobbin shape. Therefore, the alternating magnetic flux output from power transmitting coil 111 is easily collected by magnetic core 63. That is, a magnetic flux passing through the core of the bobbin shape is bent through a collar portion of magnetic core 63. Therefore, the flux is easily returned to power transmitting coil 111. Accordingly, leakage of a magnetic flux is prevented, and a coupling degree of coupling coefficient of power transmitting coil 111 and magnetism collecting coil 71 increases. As a result, a decrease in power transmission efficiency can be prevented.

As described above, in noncontact power supply device 1 according to the present exemplary embodiment, center TCC of power transmitting coil 111 and center RCC of magnetism collecting coil 71 are disposed in a shifted manner. Accordingly, the above operation and advantageous effects are obtained.

Operation and advantageous effects in the configuration of power receiving unit 61 of power reception device 60 will be described below with reference to FIG. 31 and FIG. 32, while comparing the operation and advantageous.

Figure 31:
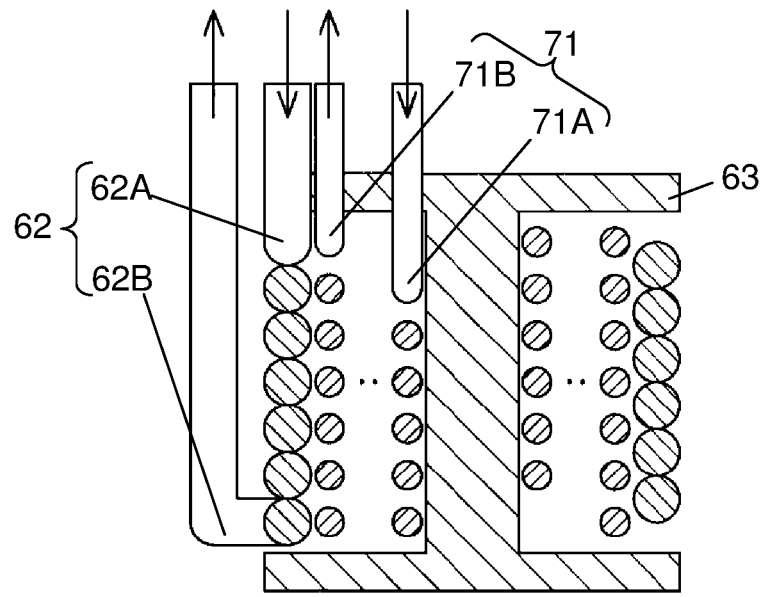
FIG. 31 is a cross-sectional view schematically showing a power receiving unit in FIG. 20.

In power receiving unit 61 according to the present exemplary embodiment, first, magnetism collecting coil 71 is wound around bobbin-shaped magnetic core 63, as shown in FIG. 31. Then, by winding power receiving coil 62 around an outer periphery of magnetism collecting coil 71, with an insulation tape interposed between the coils, power receiving unit 61 is configured, for example.

In this case, even when a number of turns of power receiving coil 62 is set smaller than a number of turns of magnetism collecting coil 71, an influence to power transmission efficiency is small.

On the other hand, from the viewpoint of transmission efficiency, magnetism collecting coil 71, it is preferable that a Q value that is a characteristic value of the coil is large. A Q value is expressed by "ωL/r" (r represents a resistance value). Therefore, it is preferable to make the Q value large by making inductance L large by increasing the number of turns of magnetism collecting coil 71.

Therefore, according to the present exemplary embodiment, first, magnetism collecting coil 71 is wound around magnetic core 63 by overlapping of even number time, for example, by double. Then, power receiving coil 62 is wound by one-fold around the outer periphery of magnetism collecting coil 71 which is wound around magnetic core 63. Accordingly, power receiving unit 61 is configured. In this case, because power receiving coil 62 is wound by one-fold around the outer periphery of magnetism collecting coil 71, winding start part 62A and winding end part 62B are exposed to an outside of power receiving unit 61. Therefore, power receiving coil 62 can be easily connected to each external element. Further, because magnetism collecting coil 71 is wound by overlapping of an even number time, winding start part 71A and winding end part 71B can be disposed on the same side in the axial direction. Therefore, winding start part 71A and winding end part 71B of magnetism collecting coil 71 can be easily pulled outside of power receiving unit 61. Accordingly, winding start part 71A and winding end part 71B of magnetism collecting coil 71 are easily connected to each external element.

Next, a configuration of magnetism collecting coil 71 and power receiving coil 62 of power receiving unit 161 shown as a comparative example will be described with reference to FIG. 32.

Figure 32:
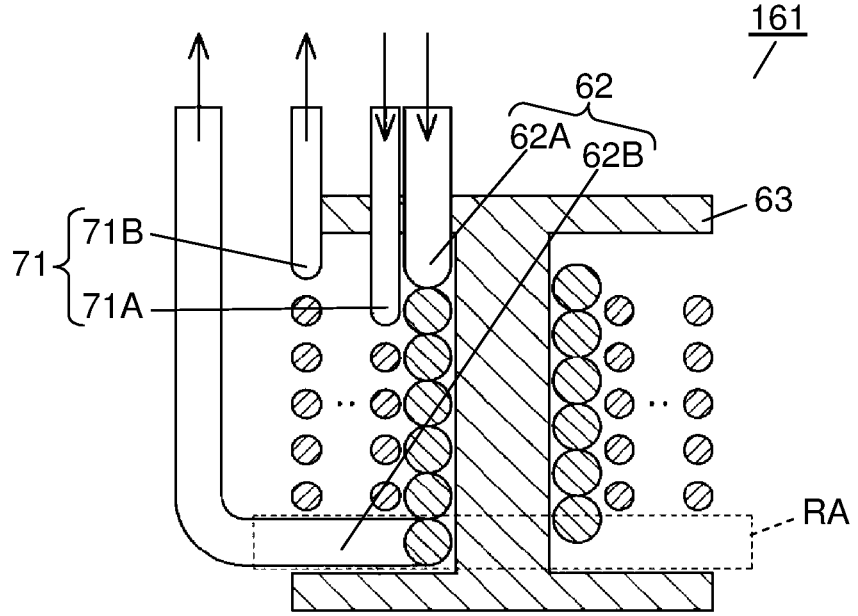
FIG. 32 is a cross-sectional view schematically showing a power receiving unit of a comparative example.

For power receiving unit 161 shown in FIG. 32, first, power receiving coil 62 is wound around bobbin-shaped magnetic core 63 by one-fold. Then, by winding magnetism collecting coil 71 around the outer periphery of power receiving coil 62 by overlapping of an even number time, power receiving unit 161 is configured. In this case, winding start part 62A and winding end part 62B of power receiving coil 62 are disposed on opposite sides in the axial direction. Therefore, region RA for pulling out winding end part 62B of power receiving coil 62 needs to be formed on winding end part 62B side. Accordingly, in the case of magnetic core 63 of the same shape as that in FIG. 31, a region in which magnetism collecting coil 71 can be wound becomes small. As a result, the number of turns of magnetism collecting coil 71 becomes small. Further, because power receiving coil 62 is not wound by multiple turns, the outer diameter can be made small.

That is, for power receiving unit 61 shown in FIG. 31, magnetism collecting coil 71 is wound around bobbin-shaped magnetic core 63, and power receiving coil 62 is wound around the outer periphery of magnetism collecting coil 71. Therefore, it is not necessary to form region RA, unlike power receiving unit 161 of the comparative example shown in FIG. 32. Accordingly, reduction in the number of turns of magnetism collecting coil 71 can be prevented. As a result, a Q value of magnetism collecting coil 71 can be increased.

Effects of noncontact power supply device 1 configured as described above will be described in detail by listing.

(1) Because magnetism collecting device 70 is not electrically connected to rechargeable battery 41, a Q value can be easily set larger than that of power receiving coil 62. Then, a magnetic flux output from power transmitting coil 111 is interlinked with magnetism collecting coil 71, and a magnetic flux output from magnetism collecting coil 71 is interlinked with power receiving coil 62. Accordingly, power transmission efficiency can be more increased than when magnetism collecting device 70 does not exist.

(2) Usually, a noncontact power supply device including a magnetism collecting circuit can further increase power transmission efficiency, when drive frequency fD and power-transmission resonance frequency f1 of each switching element are substantially coincided with power-reception resonance frequency f2 of a magnetism collecting circuit. However, in order to make frequencies fD, f1, f2 coincide with each other, high precision adjustment becomes necessary. Therefore, there is a concern about reduction in productivity of a noncontact power supply device. Therefore, in noncontact power supply device 1 according to the present exemplary embodiment, frequencies fD, f1, f2 are set to mutually different values. Therefore, it is not necessary to make frequencies fD, f1, f2 coincide with each other. Accordingly, even when there are variations such as manufacturing errors (tolerance) in the components, high precision adjustment becomes unnecessary. As a result, it is possible to increase productivity of noncontact power supply device 1.

Further, power-transmission resonance frequency f1 is set smaller than drive frequency fD. Therefore, as compared with a case where power-transmission resonance frequency f1 is higher than drive frequency fD, operations of first switching element 112A and second switching element 112B are stabilized. That is, when power-transmission resonance frequency f1 is set smaller than drive frequency fD, inductive resonance occurs in a resonant circuit. Therefore, noise (ringing of a current) does not easily occur, and an operation becomes stable. Accordingly, power transmission efficiency does not easily decrease.

Further, when power-reception resonance frequency f2 is larger than drive frequency fD, stable output can be obtained against a variation in a load, as compared with a case where power-reception resonance frequency f2 is smaller than drive frequency fD. The inventors of the present invention have confirmed this effect by tests.

By the above, noncontact power supply device 1 with high power transmission efficiency and with excellent productivity can be realized.

(3) Usually, when a difference between drive frequency fD and power-transmission resonance frequency f1 is smaller, power transmission efficiency can be increased. In noncontact power supply device 1 according to the present exemplary embodiment, a lower limit (85%) of power-transmission resonance frequency f1 is prescribed. Therefore, high power transmission efficiency can be secured.

(4) In noncontact power supply device 1 according to the present exemplary embodiment, even when a coupling coefficient is included in any one of a first range and a second range which are mutually different, or even when the body is not disposed in the power transmission device, a large and small relationship between drive frequency fD of first switching element 112A and second switching element 112B and power-transmission resonance frequency f1 is maintained. Therefore, the influence of an arrangement position of magnetism collecting device 70 in power transmission device 110 to an influence of switching can be prevented. Accordingly, the possibility of reduction in power transmission efficiency can be reduced.

(5) In a state that center TCC of power transmitting coil 111 in the axial direction is shifted from center RCC of magnetism collecting coil 71 in the axial direction, rechargeable battery 41 as a load is charged. Therefore, as described with reference to FIG. 30, the output current can be made large as compared with the case where centers of power transmitting coil 111 and magnetism collecting coil 71 in their axial direction coincide with each other. Accordingly, noncontact power supply device 1 that can transmit larger power can be realized.

(6) Noncontact power supply device 1 according to the present exemplary embodiment includes power receiving coil 62 and magnetism collecting coil 71 that are wound around bobbin-shaped magnetic core 63 that includes a magnetic material. Therefore, a magnetic flux that interlinks with power transmitting coil 111 and magnetism collecting coil 71 does not easily leak. Accordingly, power transmission efficiency can be more increased.

Further, magnetism collecting coil 71 and power receiving coil 62 are wound around one magnetic core 63. Therefore, a configuration of noncontact power supply device 1 can be simplified.

(7) Power transmission controller 115 grasps ON time TX by measuring in advance ON time TX such that the output current (a power receiving current) of the power receiving unit is included within a predetermined range, in the transmission mode. Grasped ON time TX is stored as the first fixed value in the storage unit of power transmission controller 115. In this case, the predetermined range is a range from a permissible upper limit to lower limit of a charge current. Then, by using a first fixed value set in advance, in the transmission mode, power transmission device 110 is driven. Accordingly, it is not necessary to perform feedback based on the output current. As a result, more proper power transmission efficiency is obtained.

Further, it is not necessary to mount a circuit for feedback. Therefore, a configuration of noncontact power supply device 1 can be simplified.

Further, it is not necessary to change power-transmission resonance frequency f1 and power-reception resonance frequency f2, by using a variable capacitor. Accordingly, by avoiding use of a large-type capacitor, increase in size of noncontact power supply device 1 can be prevented. Further, it is not necessary to include a plurality of capacitors and change power-transmission resonance frequency f1 and power-reception resonance frequency f2 by changing to a proper capacitor. Accordingly, increase in size of power transmission device 110 can be prevented. That is, power transmission controller 115 controls to reduce the variation in the power-transmitting coil current flowing through power transmitting coil 111, by using one power-transmission resonant capacitor 116. Therefore, as compared with the case of using a variable capacitor or a plurality of capacitors, increase in size of noncontact power supply device 1 can be prevented.

(8) Usually, when there exists an error such as a manufacturing variation in the values of a plurality of switching elements, ON times TX necessary to include an output current (a charge current) within a predetermined range are mutually different. Therefore, power transmission controller 115 according to the present exemplary embodiment sets, individually in advance, ON times TX of first switching element 112A and second switching element 112B. Therefore, more proper power transmission efficiency is obtained. Further, by individually setting ON times TX, the power-transmitting coil current can be finely adjusted. Accordingly, even in the configuration of power transmission controller 115 with low resolution in the PWM signal, the power-transmitting coil current can be properly adjusted.

(9) Power transmission controller 115 grasps ON time TY by measuring in advance ON time TY such that the output current is included within a predetermined range, in the standby mode. Grasped ON time TY is stored as the second fixed value in the storage unit of power transmission controller 115. In this case, the predetermined range is a range of the output current prescribed for reducing the power consumption. Then, by using a second fixed value set in advance, in the standby mode, power transmission device 110 is driven. Accordingly, it is not necessary to perform feedback based on the output current. As a result, power consumption is properly reduced.

Modification

Description concerning the present exemplary embodiment illustrates a possible exemplary embodiment of the noncontact power supply device according to the present invention. Therefore, it is not intended to limit the possible exemplary embodiment of the noncontact power supply device. In other words, the noncontact power supply device according to the present invention can adopt, in addition to the present exemplary embodiment, for example, modification of the exemplary embodiment shown below, and a mode of combination of at least two modifications that are not mutually inconsistent.

That is, in the present exemplary embodiment, an example of a configuration in which ON times TX, TY are set by measurement of the output current (charge current) has been described. However, the present exemplary embodiment is not limited to this example. For example, ON times TX, TY may be set based on the input current. In this case, the ON times of the PWM signal when the input current is included in a predetermined range are set as ON times TX, TY. Then, set ON times TX, TY are stored in the storage unit of power transmission controller 115. Further, ON times TX, TY may be set based on a resonance voltage V. In this case, the ON times of the PWM signal when resonance voltage V is included in a predetermined range are set as ON times TX, TY. Then, set ON times TX, TY are stored in the storage unit of power transmission controller 115. Further, ON times TX, TY may be set based on the power-transmitting coil current of power transmitting coil 111. In this case, the ON times of the PWM signal when the power-transmitting coil current is included in a predetermined range are set as ON times TX, TY. Then, set ON times TX, TY are stored in the storage unit of power transmission controller 115. Set ON times TX, TY correspond to first ON time TXA and second ON time TXB in the transmission mode. Set ON times TX, TY correspond to first ON time TYA and second ON time TYB in the standby mode.

Further, in the present exemplary embodiment, power transmission device 110 has been described based on an example of configuring power transmission device 110 with a half-bridge circuit shown in FIG. 21. However, the present exemplary embodiment is not limited to this example. For example, power transmission device 110 may be configured by a full-bridge circuit shown in FIG. 33. In this case, power transmission device 210 includes first switching element 212A, second switching element 212B, third switching element 212C, fourth switching element 212D, smoothing capacitor 213, first drive circuit 214A, second drive circuit 214B, third drive circuit 214C, and fourth drive circuit 214D.

Figure 33:
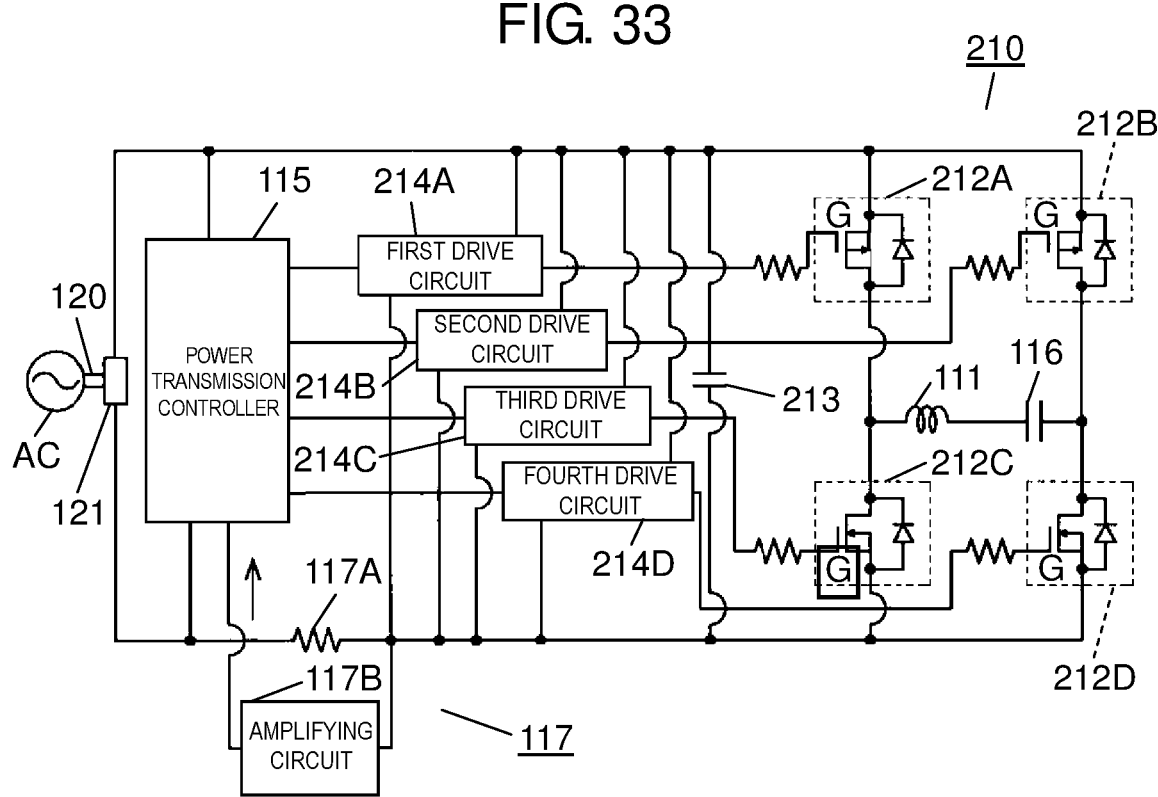
FIG. 33 is a block diagram of a modification of the power transmission device in FIG. 21.
Figure 34:
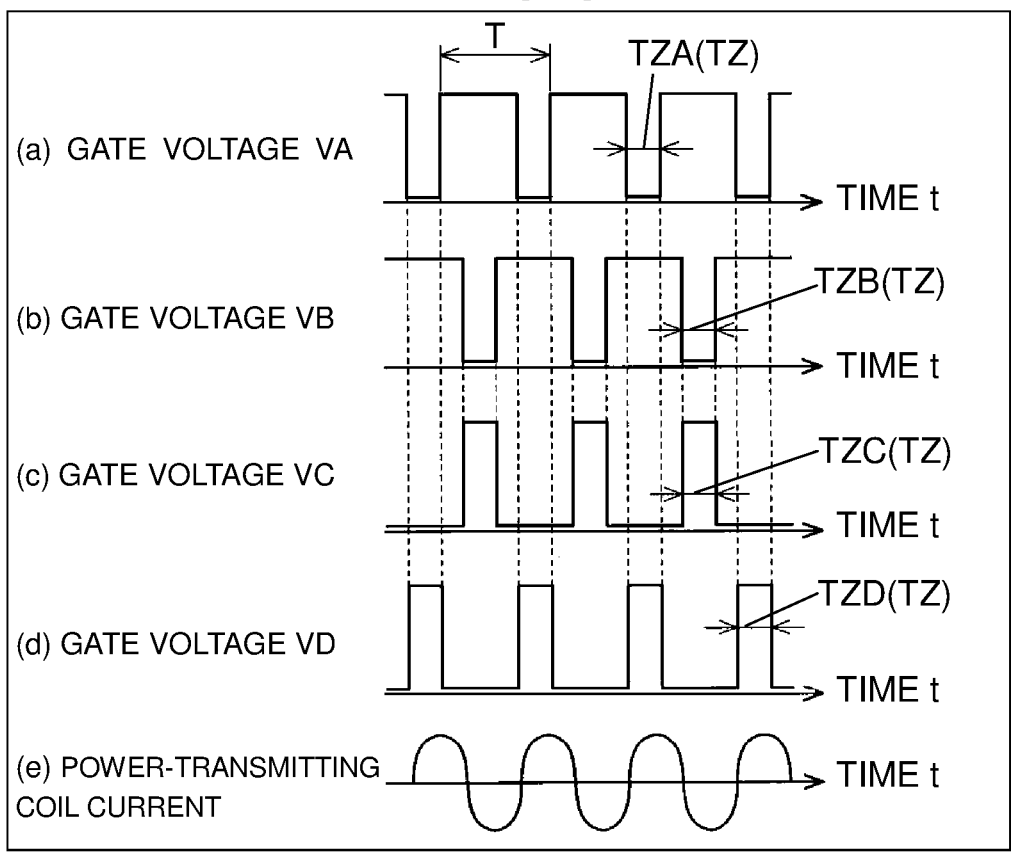
FIG. 34 is a timing chart showing an example of control of the switching elements which is performed by the power transmission controller of the power transmission device according to the modification in FIG. 33.

Then, in power transmission device 210 shown in FIG. 33, ON time TZ of a PWM signal to be input to gate G of each switching element is set, as shown in (a), (b), (c), and (d) of FIG. 34. In this case, as shown in (a) and (d) of FIG. 34, ON time TZA of first switching element 212A and ON time TZD of fourth switching element 212D are set to become equal. Similarly, as shown in (b) and (c) of FIG. 34, ON time TZB of second switching element 212B and ON time TZC of third switching element 212C are set to become equal. Accordingly, as shown in (e) of FIG. 34, a power-transmitting coil current flowing through power transmitting coil 111 of power transmission device 210 becomes in a sinusoidal waveform, for example. In the case of a full-bridge, a power source voltage becomes double, so that output can be increased.

Further, in the present exemplary embodiment, power reception device 60 has been described by taking an example that alternating power of power receiving coil 62 is half-wave rectified. However, the alternating power may be full-wave rectified. Accordingly, power loss can be reduced.

Further, in the present exemplary embodiment, power receiving coil 62 has been described by taking an example that power receiving coil 62 is disposed on an outer periphery of magnetism collecting coil 71. However, when there is margin in the space, power receiving coil 62 may be disposed on an inner periphery.

Further, in the present exemplary embodiment, magnetism collecting device 70 has been described by taking an example of a configuration that magnetism collecting device 70 is included in electric toothbrush 10 which is a small electric device. However, magnetism collecting device 70 may be configured to be included in charging stand 80. Accordingly, the body can be made compact.

Further, in the present exemplary embodiment, magnetism collecting device 70 may be omitted. In this case, in place of magnetism-collecting resonant capacitor 72, a power-reception resonant capacitor is connected to power receiving coil 62. Then, a power-reception resonant circuit is configured by power receiving coil 62 and a power-reception resonant capacitor. In this case, a resonance frequency of a power-reception resonant circuit including power receiving coil 62 and a power-reception resonant capacitor corresponds to power-reception resonance frequency f2. Accordingly, a number of components can be reduced.

Further, in the present exemplary embodiment, magnetic core 63 may be formed in a rod shape. Further, by omitting magnetic core 63, power receiving coil 62 and magnetism collecting coil 71 may be configured by fixing by heat-welding. Accordingly, the body can be made compact.

The noncontact power supply device according to the present exemplary embodiment may be applied to a noncontact power supply device that includes an oral cleaning machine for cleaning an oral cavity by ejecting water, or a stain cleaner for removing stains by polishing teeth, a shaver, or a hair remover. Accordingly, because an electric contact becomes unnecessary, the noncontact power supply device can be safely used around water.

(An Example of a Possible Exemplary Embodiment of a Noncontact Power Supply Device)

(1) A noncontact power supply device according to one exemplary embodiment of the present invention has a power transmission device including: a power-transmission resonant circuit that outputs an alternating magnetic flux by alternating power supplied from a power source circuit; and a switching element that makes the power-transmission resonant circuit generate an alternating magnetic flux. The noncontact power supply device further has: a magnetism collecting device including: a magnetism collecting circuit which is a resonant circuit which is capable of being magnetically coupled to the power-transmission resonant circuit and is not electrically connected to the load; and a power reception device including a power receiving coil which is capable of being magnetically coupled to the magnetism collecting circuit, and a rectifier circuit which is capable of supplying power output from the power reception device to the load. A power-transmission resonance frequency of the power-transmission resonant circuit may be smaller than the drive frequency of the switching element, and a power-reception resonance frequency of the magnetism collecting circuit may be larger than the drive frequency of the switching element.

According to this configuration, because the magnetism collecting circuit is not electrically connected to the load, the magnetism collecting coil of the magnetism collecting circuit is not easily affected by the load (a rechargeable battery). Therefore, unlike the power receiving coil, a Q value can be set large without depending on the load. Then, a magnetic flux output from the power transmitting coil of the power-transmission resonant circuit is interlinked with the magnetism collecting coil of the magnetism collecting circuit, and a magnetic flux output from the magnetism collecting coil is interlinked with the power receiving coil. Accordingly, transmission of power from the power transmitting coil of the power-transmission resonant circuit to the magnetism collecting coil of the magnetism collecting circuit can be performed based on the high Q value. Further, the increase in the Q value contributes to increase power transmission efficiency. Therefore, for example, even when the power transmitting coil of the power-transmission resonant circuit and the magnetism collecting coil of the magnetism collecting circuit are disposed apart from each other and the coupling coefficient is small, power can be transmitted based on the high Q value. Accordingly, as compared with a case of a configuration in which a magnetism collecting circuit is not provided, power transmission efficiency can be increased.

Usually, in a noncontact power supply device including a magnetism collecting circuit, when the drive frequency of the switching element and resonance frequencies of all resonant circuits concerning the transmission of power are substantially coincided with each other, power transmission efficiency can be further increased. However, in order to make the frequencies coincide with each other, high precision adjustment becomes necessary. Therefore, there is a concern about reduction in productivity of a noncontact power supply device. According to the noncontact power supply device in the above configuration, frequencies are set in values of mutually different magnitudes. Therefore, it is not necessary to make frequencies coincide with each other. Accordingly, even when there are variations such as manufacturing errors (tolerance) in the components, high precision adjustment becomes unnecessary. As a result, it is possible to increase productivity of noncontact power supply device 1.

Further, the power-transmission resonance frequency of the power-transmission resonant circuit is set smaller than the drive frequency of the switching element. Therefore, as compared with a case where the power-transmission resonance frequency is higher than the drive frequency, the operation of the switching element is stabilized. Accordingly, power transmission efficiency does not easily decrease.

When the power-reception resonance frequency of the magnetism collecting circuit is larger than the drive frequency of the switching element, stable output can be obtained against a load variation, as compared with a case where the power-reception resonance frequency of the magnetism collecting circuit is smaller.

From the above, a noncontact power supply device with high power transmission efficiency and with excellent productivity can be realized.

(2) In the noncontact power supply device according to one exemplary embodiment of the present invention, the power-reception resonance frequency of the magnetism collecting circuit may be in a range exceeding the drive frequency of the switching element and equal to or less than 115% of the drive frequency.

Usually, when a difference between the drive frequency of a switching element and a power-reception resonance frequency of a magnetism collecting circuit is smaller, power transmission efficiency can be increased. That is, according to the above configuration, an upper limit of the power-reception resonance frequency of the magnetism collecting circuit is prescribed. Therefore, high power transmission efficiency can be secured.

(3) In the noncontact power supply device according to one exemplary embodiment of the present invention, the power-transmission resonance frequency of the power-transmission resonant circuit may be in a range less than the drive frequency of the switching element and equal to or higher than 85% of the drive frequency.

(4) In the noncontact power supply device according to one exemplary embodiment of the present invention, the power-transmission resonant circuit of a power-transmission resonant circuit may be smaller than the drive frequency of the switching element in any one of a case where when a power transmitting coil and a magnetism collecting coil are disposed closely, a coupling coefficient is included in a first range, a case where when the power transmitting coil and the magnetism collecting coil are disposed apart from each other, a coupling coefficient is included in a second range smaller than the first range, and a case where a body is not disposed in the power transmission device.

According to this configuration, a large and small relationship between the drive frequency of the switching element and the power-transmission resonance frequency of the power-transmission resonant circuit is maintained, even when the coupling coefficient determined by the disposition relationship between the power transmitting coil and the magnetism collecting coil of which coupling coefficients are different is included in the first range or the second range, or when the body is not disposed in the power transmission device. Therefore, the possibility of reduction in power transmission efficiency due to the influence of an arrangement position of the magnetism collecting device relative to the power transmission device can be reduced.

(5) In a noncontact power supply device according to one exemplary embodiment of the present invention, the power transmission device further includes a support part which is capable of supporting a magnetism collecting device. The support part may be configured to support the magnetism collecting device such that at least parts of the power transmitting coil of the power-transmission resonant circuit and the magnetism collecting coil of the magnetism collecting circuit are superposed in the axial direction and that a center of the power transmitting coil in an axial direction and a center of the magnetism collecting coil in an axial direction are shifted.

According to this configuration, the output current can be made larger than when the centers in the axial direction of the power transmitting coil of the power-transmission resonant circuit and the magnetism collecting coil of the magnetism collecting circuit coincide with each other. Therefore, larger power can be transmitted.

(6) In a noncontact power supply device according to one exemplary embodiment of the present invention, the power reception device may include a magnetism collecting device, and the power reception device may further include a core around which the power receiving coil and the magnetism collecting coil are wound. Accordingly, a power receiving coil and a magnetism collecting coil are wound around one core. Therefore, a configuration of noncontact power supply device 1 can be simplified.

(7) In a noncontact power supply device according to one exemplary embodiment of the present invention, the core may be formed of a magnetic body.

According to this configuration, the noncontact power supply device includes the core formed of the magnetic body. Therefore, the coupling between the power transmitting coil of the power-transmission resonant circuit and the magnetism collecting coil of the magnetism collecting circuit can be increased. Further, a variation in the power-transmission resonance frequency depending on a position of the magnetism collecting coil of the magnetism collecting circuit can be made large. Therefore, an adjustment width of output can be increased.

(8) In a noncontact power supply device according to one exemplary embodiment of the present invention, the core may have a bobbin shape.

According to this configuration, a magnetic flux interlinked with the power receiving coil and the magnetism collecting coil of the magnetism collecting circuit does not leak easily. Therefore, power transmission efficiency can be increased more.

(9) A noncontact power supply device according to one exemplary embodiment of the present invention has: a power transmission device including a power-transmission resonant circuit that outputs an alternating magnetic flux by alternating power supplied from a power source circuit, and a switching element that makes the power-transmission resonant circuit generate an alternating magnetic flux; and a power reception device including a power receiving coil which is capable of being magnetically coupled to the power-transmission resonant circuit, and a rectifier circuit which is capable of supplying power output from the power receiving coil to a load. Further, a power-transmission resonance frequency of the power-transmission resonant circuit may be smaller than the drive frequency of the switching element, and a power-reception resonance frequency of the power-reception resonant circuit including the power receiving coil may be larger than the drive frequency of the switching element. Accordingly, an effect similar to that in (1) is obtained.

(10) In a noncontact power supply device according to one exemplary embodiment of the present invention, the power-reception resonance frequency of the power receiving coil may be in a range exceeding the drive frequency of the switching element and equal to or less than 115% of the drive frequency. Accordingly, an effect similar to that in (2) is obtained.

(11) In a noncontact power supply device according to one exemplary embodiment of the present invention, the power-transmission resonance frequency of the power-transmission resonant circuit may be in a range less than the drive frequency of the switching element and is equal to or higher than 85% of the drive frequency. Accordingly, an effect similar to that in (3) is obtained.

Note (1)

A noncontact power supply device including: a power transmission device including a power-transmission resonant circuit that outputs an alternating magnetic flux by alternating power supplied from a power source circuit, and a plurality of switching elements that are switched so that an alternating magnetic flux is generated in the power-transmission resonant circuit; a magnetism collecting device including a magnetism collecting circuit which is capable of being magnetically coupled to the power-transmission resonant circuit and is not electrically connected to a load; and a power reception device including a power receiving coil which is capable of being magnetically coupled to the magnetism collecting circuit, and a rectifier circuit which is capable of supplying power output from the power receiving coil, to the load, wherein a coupling coefficient between the power transmitting coil and a coil of the magnetism collecting circuit in a state that the magnetism collecting device is supported by the support part is equal to or higher than 0.2.

Note (2)

The noncontact power supply device according to Note (1), wherein a shift quantity between a center in an axial direction of the coil of the power-transmission resonant circuit and a center in an axial direction of the coil of the magnetism collecting circuit is about a half of a length in an axial direction concerning the coil of the power-transmission resonant circuit.

Note (3)

The noncontact power supply device according to Note (1) or Note (2), wherein the power reception device includes the magnetism collecting device, the power reception device further includes a bobbin formed of a magnetic body, around which the power receiving coil and the coil of the magnetism collecting circuit are wound, and the coil of the magnetism collecting circuit is wound around the bobbin, and the power receiving coil is wound around an outer periphery of the coil.

Industrial Applicability

The present invention can be applied to various kinds of noncontact power supply devices that are used in homes, medical organizations, or equivalent environments.

REFERENCE MARKS IN THE DRAWINGS

1: noncontact power supply device
10: electric toothbrush
11: head
20: body
21: case
22: grip part
23: supported part
23A: protrusion
24: display unit
24A: ion display unit
24B: drive-mode display unit
24C: residual-quantity display unit
24D: charge display unit
25: power source button
26: upper cap
26A, 27C: front cap
26B, 27B: inner cap
26C: coupling part
26D: hole
27: lower cap
27A: bottom surface
28A, 28B, 28C, 28D: elastic member 29: support body
29A: hook
30: drive unit
31: output shaft
40: power source unit
41: rechargeable battery (load)
42: metal plate
50, 100: substrate
51: lead frame
60: power reception device
61, 161: power receiving unit
62: power receiving coil
62A, 71A: winding start part
62B, 71B: winding end part
63: magnetic core (core)
64: diode (rectifier circuit)
65, 213: smoothing capacitor
66, 117: current detecting circuit
66A, 117A, 118A, 118B: resistor
66B, 117B: amplifying circuit
67: power reception controller
68: switch
69: timing detecting circuit
70: magnetism collecting device
71: magnetism collecting coil
72: magnetism-collecting resonant capacitor
80: charging stand
81: case
82: base
82A: top plate
82B: top surface
82C: bottom plate
82D: bottom surface
83: pillar
84: support part
84A: hole
84B: recess
84C: guide part
90: connection part
91, 123: large diameter part
92, 122: small diameter part
93: terminal
101: lead wire
110, 210: power transmission device
111: power transmitting coil
112A, 212A: first switching element
112B, 212B: second switching element
113A, 113B: capacitor
114A, 214A: first drive circuit
114B, 214B: second drive circuit
115: power transmission controller
116: power-transmission resonant capacitor
118: voltage detecting circuit
120: power source line
121: power source circuit
212C: third switching element
212D: fourth switching element
214C: third drive circuit
214D: fourth drive circuit

The invention claimed is:

1. A noncontact power supply device comprising:
a power transmission device including a power-transmission resonant circuit that outputs an alternating magnetic flux by alternating power supplied from a power source circuit, and a switching element that makes the power-transmission resonant circuit generate an alternating magnetic flux;
a magnetism collecting device including a magnetism collecting circuit configuring a magnetism-collecting resonant circuit which is capable of being magnetically coupled to the power-transmission resonant circuit and is not electrically connected to a load; and
a power reception device including a power receiving coil which is capable of being magnetically coupled to the magnetism collecting circuit, and a rectifier circuit which is capable of supplying power output from the power receiving coil, to the load,
wherein a power-transmission resonance frequency of the power-transmission resonant circuit is smaller than a drive frequency of the switching element, and a power-reception resonance frequency of the magnetism collecting circuit is larger than the drive frequency of the switching element.

2. The noncontact power supply device according to claim 1, wherein the power-reception resonance frequency of the magnetism collecting circuit is in a range exceeding of the drive frequency of the switching element and equal to or less than 115% of the drive frequency.

3. The noncontact power supply device according to claim 1, wherein the power-transmission resonance frequency of the power-transmission resonant circuit is in a range less than the drive frequency of the switching element and equal to or higher than 85% of the drive frequency.

4. The noncontact power supply device according to claim 1, wherein the power-transmission resonance frequency of the power-transmission resonant circuit is smaller than the drive frequency of the switching element in any one of a case where when a power transmitting coil and a magnetism collecting coil are disposed closely, a coupling coefficient is included in a first range, a case where when the power transmitting coil and the magnetism collecting coil are disposed apart from each other, a coupling coefficient is included in a second range smaller than the first range, and a case where a body is not disposed in the power transmission device.

5. The noncontact power supply device according to claim 1, wherein the power transmission device further includes a support part which is capable of supporting the magnetism collecting device, and the support part supports the magnetism collecting device such that at least parts of a power transmitting coil of the power-transmission resonant circuit and a magnetism collecting coil of the magnetism collecting circuit are superposed in an axial direction and that a center of the power transmitting coil in an axial direction and a center of the magnetism collecting coil in an axial direction are shifted.

6. The noncontact power supply device according to claim 1, wherein the power reception device includes the magnetism collecting device, and the power reception device further includes a core around which the power receiving coil and the magnetism collecting coil are wound.

7. The noncontact power supply device according to claim 6, wherein the core is formed of a magnetic body.

8. The noncontact power supply device according to claim 7, wherein the core has a bobbin shape.

9. A noncontact power supply device comprising:
a power transmission device including a power-transmission resonant circuit that outputs an alternating magnetic flux by alternating power supplied from a power source circuit, and a switching element that makes the power-transmission resonant circuit generate an alternating magnetic flux; and
a power reception device including a power receiving coil which is capable of being magnetically coupled to the power-transmission resonant circuit, and a rectifier circuit which is capable of supplying power output from the power receiving coil, to a load, wherein a power-transmission resonance frequency of the power-transmission resonant circuit is smaller than a drive frequency of the switching element, and a power-reception resonance frequency of a power-reception resonant circuit including the power receiving coil is larger than the drive frequency of the switching element.

10. The noncontact power supply device according to claim 9, wherein the power-reception resonance frequency of the power receiving coil is in a range exceeding the drive frequency of the switching element and equal to or less than 115% of the drive frequency.

11. The noncontact power supply device according to claim 9, wherein the power-transmission resonance frequency of the power-transmission resonant circuit is in a range less than the drive frequency of the switching element and is equal to or higher than 85% of the drive frequency.

* * * * *